(12) United States Patent
Ding et al.

(10) Patent No.: US 11,077,051 B2
(45) Date of Patent: Aug. 3, 2021

(54) SHEAR-THINNING THERAPEUTIC COMPOSITION, AND RELATED METHODS

(71) Applicant: University of Pittsburgh—Of the Commonwealth System of Higher Education, Pittsburgh, PA (US)

(72) Inventors: Xiaochu Ding, Pittsburgh, PA (US); Jin Gao, Pittsburgh, PA (US); Yadong Wang, Ithaca, NY (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 5 days.

(21) Appl. No.: 16/333,627

(22) PCT Filed: Sep. 15, 2017

(86) PCT No.: PCT/US2017/051791
§ 371 (c)(1),
(2) Date: Mar. 15, 2019

(87) PCT Pub. No.: WO2018/053273
PCT Pub. Date: Mar. 22, 2018

(65) Prior Publication Data
US 2019/0216724 A1    Jul. 18, 2019

Related U.S. Application Data

(60) Provisional application No. 62/394,991, filed on Sep. 15, 2016.

(51) Int. Cl.
| | | |
|---|---|---|
| A61K 9/00 | (2006.01) | |
| A61L 27/54 | (2006.01) | |
| A61K 31/727 | (2006.01) | |
| A61K 38/18 | (2006.01) | |
| A61L 27/20 | (2006.01) | |
| A61L 27/44 | (2006.01) | |
| A61L 27/10 | (2006.01) | |
| A61K 9/06 | (2006.01) | |
| A61K 47/36 | (2006.01) | |
| A61K 47/02 | (2006.01) | |
| C08J 3/075 | (2006.01) | |
| A61L 27/50 | (2006.01) | |
| A61K 47/24 | (2006.01) | |
| A61L 27/52 | (2006.01) | |

(52) U.S. Cl.
CPC .............. *A61K 9/0024* (2013.01); *A61K 9/06* (2013.01); *A61K 31/727* (2013.01); *A61K 38/1825* (2013.01); *A61K 47/02* (2013.01); *A61K 47/24* (2013.01); *A61K 47/36* (2013.01); *A61L 27/10* (2013.01); *A61L 27/20* (2013.01); *A61L 27/446* (2013.01); *A61L 27/50* (2013.01); *A61L 27/52* (2013.01); *A61L 27/54* (2013.01); *C08J 3/075* (2013.01); *A61L 2300/414* (2013.01); *A61L 2400/06* (2013.01); *A61L 2430/34* (2013.01); *C08J 2305/10* (2013.01)

(58) Field of Classification Search
CPC ...... A61L 27/446; A61L 27/50; A61K 9/0024
See application file for complete search history.

(56) References Cited

U.S. PATENT DOCUMENTS

| | | |
|---|---|---|
| 6,333,054 B1 | 12/2001 | Rogozinski |
| 7,537,781 B2 | 5/2009 | Richard |
| 8,257,745 B2 | 9/2012 | Ketelson et al. |
| 8,367,117 B2 | 2/2013 | Rafailovich et al. |
| 9,827,321 B2 | 11/2017 | Burdick et al. |
| 10,034,958 B2 | 7/2018 | Gaharwar et al. |
| 2005/0181014 A1 | 8/2005 | Richard |
| 2005/0181015 A1 | 8/2005 | Zhong |
| 2005/0281758 A1* | 12/2005 | Dodd ................... A61Q 11/00 424/49 |
| 2006/0088566 A1 | 4/2006 | Parsonage et al. |
| 2006/0148958 A1* | 7/2006 | Haraguchi ............ C08K 3/346 524/445 |
| 2017/0043058 A1* | 2/2017 | Oreffo .................. C08K 3/346 |

FOREIGN PATENT DOCUMENTS

| | | |
|---|---|---|
| WO | 2014028209 A1 | 2/2014 |
| WO | 2014205261 A1 | 12/2014 |

OTHER PUBLICATIONS

Ding, X. et al. "Ashear-thinning hydrogel that extends in vivo bioactivity of FGF2", Biomaterials 111 (2016) 80-89. (Year: 2016).*
Barakat et al., "VEGF inhibitors for the treatment of neovascular age-related macular degeneration", Expert Opinion on Investigational Drugs, 2009, pp. 637-646, vol. 18, No. 5.
Bhatnagar et al., "Hyaluronic Acid and Gelatin Clay Composite Hydrogels: Substrates for Cell Adhesion and Controlled Drug Delivery", Journal of Chemical and Biological Interfaces, 2014, pp. 1-11, vol. 2, No. 1.
BYK Additives & Instruments, "Laponite Performance Additives", Technical Information B-RI 21, 2014 Germany.
Carretero, "Clay materials and their beneficial effects upon human health. A review", Applied Clay Science, 2002, pp. 155-163, vol. 21.
Chappelow et al., "Neovascular Age-Related Macular Degeneration: Potential Therapies", Drugs, 2008, pp. 1029-1036, vol. 68, No. 8.
Chu et al., "Injectable fibroblast growth factor-2 coacervate for persistent angiogenesis", Proceedings of the National Academy of Sciences of the United States, 2011, pp. 13444-13449, vol. 108, No. 33.
Cummins, "Liquid, glass, gel: The phases of colloidal LAPONITE", Journal of Non-Crystalline Solids, 2007, pp. 3891-3905, vol. 353.
Dawson et al., "Clay Gels for the Delivery of Regenerative Microenvironments", Advanced Materials, 2011, pp. 3304-3308, vol. 23.

(Continued)

*Primary Examiner* — Gina C Justice
(74) *Attorney, Agent, or Firm* — The Webb Law Firm

(57) ABSTRACT

A shear-thinning therapeutic composition is provided along with methods of making and using the therapeutic composition.

20 Claims, 8 Drawing Sheets

(56) References Cited

OTHER PUBLICATIONS

Dawson et al., "Clay: New Opportunities for Tissue Regeneration and Biomaterial Design", Advanced Materials, 2013, pp. 4069-4086, vol. 25.

Gaharwar et al., "Highly Extensible Bio-Nanocomposite Films with Direction-Dependent Properties", Advanced Functional Materials, 2010, pp. 429-436, vol. 20.

Gaharwar et al., "Assessment of using Laponite® cross-linked poly(ethylene oxide) for controlled cell adhesion and mineralization", Acta Biomaterialia, 2011, pp. 568-577, vol. 7.

Gaharwar et al., "Bioactive Silicate Nanoplatelets for Osteogenic Differentiation of Human Mesenchymal Stem Cells", Advanced Materials, 2013, pp. 3329-3336, vol. 25.

Gaharwar et al., "Shear-Thinning Nanocomposite Hydrogels for the Treatment of Hemorrhage", ACS Nano, 2014, pp. 9833-9842, vol. 8, No. 10.

Gesslbauer et al., "Exploring the glycosaminoglycan-protein interaction network by glycan-mediated pull-down proteomics", Electrophoresis, 2016, pp. 1437-1447, vol. 37.

Ghadiri et al., "Laponite clay as a carrier for in situ delivery of tetracycline", RSC Advances, 2013, pp. 20193-20201, vol. 3.

Ghadiri et al., "Antibiotic eluting clay mineral (Laponite®) for wound healing application: an in vitro study", Journal of Materials Science: Materials in Medicine, 2014, pp. 2513-2526, vol. 25.

Ghadiri et al., "Layered silicate clay functionalized with amino acids: wound healing application", RSC Advances, 2014, pp. 35332-35343, vol. 4.

Ghadiri et al., "Biomedical applications of cationic clay minerals", RSC Advances, 2015, pp. 29467-29481, vol. 5.

Goncalves et al., "Antitumor Efficacy of Doxorubicin-Loaded Laponite/Alginate Hybrid Hydrogels", Macromolecular Bioscience, 2014, pp. 110-120, vol. 14.

Goncalves et al., "pH-sensitive Laponite®/doxorubicin/alginate nanohybrids with improved anticancer efficacy", Acta Biomaterialia, 2014, pp. 300-307, vol. 10.

Gupta et al., "Human Studies of Angiogenic Gene Therapy", Circulation Research, 2009, pp. 724-736, vol. 105.

Guvendiren et al., "Shear-thinning hydrogels for biomedical applications", Soft Matter, 2012, pp. 260-272, vol. 8.

Gao et al., "Chemical Structures and Bioactivities of Sulfated Polysaccharides from Marine Algae", 2011, Marine Drugs, pp. 196-223, vol. 9.

Kaunitz, "Analysis of Laponite and Heparin Hydrogel", Biomaterials Foundry, 2015, pp. 1-2, retrieved from http://www.engineering.pitt.edu/departments/bioengineering/_Documents/undergraduate-research/intramural-internships/(2161)—Fall2015/kaunitz_chloe/.

Li et al., "pH sensitive LAPONITE/alginate hybrid hydrogels: swelling behaviour and release mechanism", Soft Matter, 2011, pp. 6231-6238, vol. 7.

Liu et al., "Laponite® and Laponite®-PEO hydrogels with enhanced elasticity in phosphate-buffered saline", Polymers for Advanced Technologies, 2015, pp. 874-879, vol. 26.

Mongondry et al., "Influence of pyrophosphate or polyethylene oxide on the aggregation and gelation of aqueous laponite dispersions", Journal of Colloid and Interface Science, 2004, pp. 191-196, vol. 275.

Ori et al., "A Systems Biology Approach for the Investigation of the Heparin/Heparan Sulfate Interactome", The Journal of Biological Chemistry, Jun. 3, 2011, pp. 19892-19904, vol. 286, No. 22.

Wheelwright et al., "Fabrication and Characterisation of Polyaniline/Laponite based Semiconducting Organic/Inorganic Hybrid Material", Defence Science Journal, 2014, pp. 193-197, vol. 64, No. 3.

Wu et al., "Mechanically Tough Pluronic F127/Laponite Nanocomposite Hydrogels from Covalently and Physically Cross-Linked Networks", Macromolecules, 2011, pp. 8215-8224, vol. 44.

Wu et al., "Folic acid-modified laponite nanodisks for targeted anticancer drug delivery", Journal of Materials Chemistry B, 2014, pp. 7410-7418, vol. 2.

Xavier et al., "Bioactive Nanoengineered Hydrogels for Bone Tissue Engineering: A Growth-Factor-Free Approach", ACS Nano, 2015, pp. 3109-3118, vol. 9, No. 3.

Xu et al., "Diversification of the Structural Determinants of Fibroblast Growth Factor-Heparin Interactions", The Journal of Biological Chemistry, 2012, pp. 40061-40073, vol. 287, No. 47.

Xu et al., "Analysis of the fibroblast growth factor receptor (FGFR) signalling network with heparin as coreceptor: evidence for the expansion of the core FGFR signalling network", FEBS Journal, 2013, pp. 2260-2270, vol. 280.

Yang et al., "Composite Hydrogel Beads Based on Chitosan and Laponite: Preparation, Swelling, and Drug Release Behaviour", Iranian Polymer Journal, 2011, pp. 479-490, vol. 20, No. 6.

\* cited by examiner

SHEAR-THINNING THERAPEUTIC COMPOSITION, AND RELATED METHODS

CROSS REFERENCE TO RELATED APPLICATIONS

This application is the United States national phase of International Application No. PCT/US2017/051791 filed Sep. 15, 2017, and claims the benefit of U.S. Provisional Patent Application No. 62/394,991 filed Sep. 15, 2016, which is incorporated herein by reference in its entirety.

Provided herein are therapeutic compositions and related methods, specifically a shear-thinning dosage form and related methods.

Proteins are useful therapeutic agents for a variety of purposes. In the context of regenerative medicine, proteins and polypeptides play key roles in tissue regeneration by promoting cell proliferation, migration and differentiation to restore a diseased or damaged tissue. But the short half-life of exogenous proteins, particularly growth factors, limits the therapeutic efficacy if administered as free proteins. Heparin binds more than 400 proteins and peptides, and the resultant complex can stabilize proteins from proteolysis and prolong their bioactivity. However, typical heparin-protein complexes are soluble in water, making spatial and temporal control of delivery difficult.

LAPONITE® has been widely used in food, cosmetic and pharmaceutical industries as additives, rheological modifier or active ingredients. LAPONITE® is able to generate a stable nanoplatelet dispersion with uniform particle size (25 nm diameter and 0.92 nm thickness), large surface area ($>350$ m$^2$ g$^{-1}$), specific surface charges and certain bioactive properties (Gaharwar A K, et al., Adv Mater. 2013; 25:3329-36 and Dawson J I, et al. Clay gels for the delivery of regenerative microenvironments. Adv Mater. 2011; 23:3304-8). For example, in several recent reports, in vitro studies showed that the LAPONITE® dispersion or gel could facilitate chondrogenic differentiation of human bone marrow stromal cells (hBSMCs) or promote osteogenetic differentiation of human mesenchymal stem cells (hMSCs) (Gaharwar A K, et al., Adv Mater. 2013; 25:3329-36 and Dawson J I, et al. Adv Mater. 2011; 23:3304-8). The LAPONITE® dispersion can self-organize into "house-of-cards" gel through face-to-edge interaction with gelation rate dependent on its concentration (See FIG. 1).

Such LAPONITE® dispersion can either directly absorb biomolecules for delivery or complex with other synthetic or natural biopolymers to form injectable nanocomposite hydrogels for cell or drug delivery. However, when it is used for controlled release of bioactive proteins, the strong absorption on LAPONITE® particles makes release of the proteins difficult, defeating the purpose of controlled release. Though many biomaterials, such as alginate, collagen, hyaluronic acid and chitosan, have been used to mix with LAPONITE® to form injectable hydrogels for drug delivery (Xavier J R, et al. Bioactive Nanoengineered Hydrogels for Bone Tissue Engineering: A Growth-Factor-Free Approach. ACSNANO. 2015; 9:3109-18, Divya Bhatnagar D X, et al. Hyaluronic Acid and Gelatin Clay Composite. Journal of Chemical and Biological Interfaces. 2014; 2:1-11; Li Y, et al. pH sensitive LAPONITE®/alginate hybrid hydrogels: swelling behaviour and release mechanism. Soft Matter. 2011; 7:6231; and Yang H, et al. Composite Hydrogel Beads Based on Chitosan and LAPONITE®: Preparation, Swelling, and Drug Release Behaviour. Iranian Polymer Journal. 2011; 20:479-90), those biomaterials cannot protect the proteins from proteolysis and prolong their bioactivity.

SUMMARY

A composition and related methods are provided herein to take advantage of the unique properties of heparin and other compositions, such as sulfated or sulfamated compositions that bind to therapeutic active agents (therapeutic agents). According to aspects, a hydrogel is provided that is assembled from silicate platelet nanoparticle (e.g., LAPONITE® or other days), a gelling agent, such as heparin, and a therapeutic agent, such as a heparin-binding angiogenic agent or growth factor, e.g., fibroblast growth factor-2 (FGF2). The gel is rapidly-assembled, for example within one minute—resulting in a shear thinning hydrogel comprising a three-dimensional nanocomposite network formed in aqueous solution based on non-covalent reversible crosslinks.

In aspects, the shear thinning hydrogel is designed to bear functional moieties for forming physical, non-covalent crosslinks, such as hydrogen bonding, ionic interaction, host-guest chemistry, hydrophobic interaction or combination of multiple physical interactions in one system. Gelling agents such as biopolymers, for example and without limitation sulfated or sulfamated polysaccharides or sulfated or sulfamated glycosaminoglycans, can directly bind to silica nanoparticles, such as LAPONITE® platelets, to generate injectable hydrogels. The interaction between the gelling agent and the day particles form injectable hydrogels having a large surface area, specific surface charges and strong binding abilities to a variety of therapeutic agents, such as proteins, peptides, and oligopeptides. In contrast to covalently-crosslinked injectable hydrogels, shear thinning hydrogels are also injectable but do not need any triggers to initiate a chemical reaction for in situ gelation—which can exhibit toxicity to the surrounding tissues by virtue of the cross-linkers and/or the crosslinking chemistries. In the described compositions, the drugs, e.g., biologics, peptides, proteins, oligopeptides, peptide nucleic acids, or nucleic acids, can be fully loaded into a shear thinning gel and the gel-sol transition during injection occurs only at the interface between the hydrogel and needle wall. Thus the drug is less likely to leak out, leading to more precise control over dosage and release kinetics of the drug.

According to one aspect, a shear-thinning therapeutic composition is provided. In one aspect, the shear-thinning therapeutic composition comprises: silicate platelets; a gelling agent non-covalently linking the platelets to form a shear-thinning composition; and a therapeutic agent that binds non-covalently to the gelling agent and that is complexed non-covalently with the gelling agent.

In other aspects, the composition comprises natural or synthetic silicate platelets (e.g., LAPONITE®); a sulfated or sulfamated polymer non-covalently linking the platelets to form a shear-thinning composition; and a therapeutic agent that is binding partner of the sulfated or sulfamated polymers or oligomers complexed non-covalently with the sulfated or sulfamated polymers or oligomers. Optionally, the composition comprises natural or synthetic silicate platelets; a gelling agent that is one or more of a cationic amino acid; an anionic amino acid; a hydrophilic amino acid; and a polypeptide, optionally an oligopeptide, comprising from 2 to 10 amino acids or from 2 to 6 amino acids and including a plurality of cationic, anionic, or hydrophilic amino acids non-covalently linking the platelets to form a shear-thinning composition; and a therapeutic agent dispersed within the composition and/or complexed non-covalently with the silicate platelets and/or the one or more of a cationic amino acid; an anionic amino acid; a hydrophilic amino acid; a polypeptide, optionally an oligopeptide, comprising from 2 to 10 amino acids or from 2 to 6 amino acids and including a plurality of cationic, anionic, or hydrophilic amino acids. Methods of making the therapeutic composition, and methods of using the therapeutic composition, for example and without limitation to induce angiogenesis or as a soft tissue filler in a patient, also are provided.

DETAILED DESCRIPTION

Figure 1:
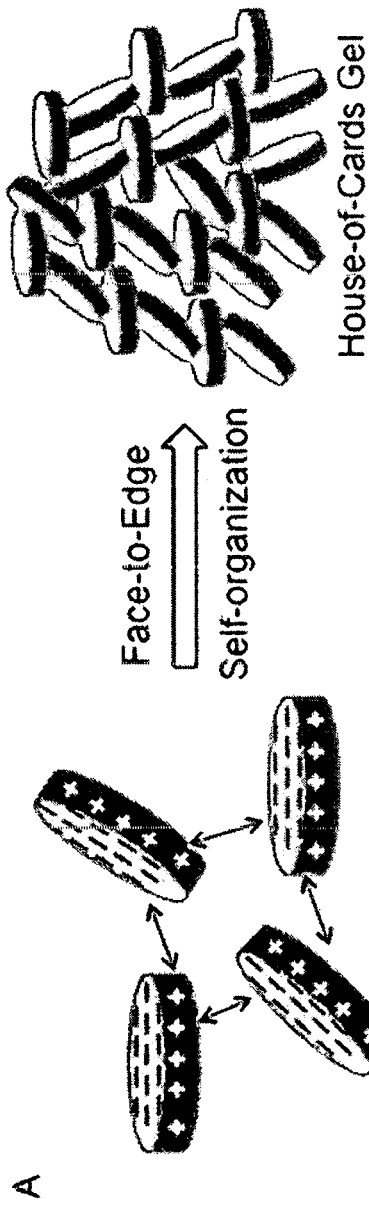
FIG. 1. (A) Schematic illustration of forming "house-of-cards" gel from LAPONITE® nanoplatelets. (B) Oscillatory time sweep and (C) angular frequency sweep measurements of LAPONITE® gels at different concentrations. (Diamond) 26.6 mg/mL, (Square) 30 mg/mL, (Circle) 35 mg/mL and (Triangle) 39.1 mg/mL. All LAPONITE® dispersions were prepared by dispersing LAPONITE® powders in deionized water with vigorously magnetic stirring for 2 h and then immediately transferred to a parallel plate for oscillatory time sweep (frequency at 1 rad/s and strain at 1%) and angular frequency sweep tests (strain at 1%) (n=3). The results indicate that gelation rate is proportional to LAPONITE® concentration. When LAPONITE® concentration is above 30 mg/mL, it can quickly form gels. The storage modulus (G') is much greater than loss modulus (G") throughout the frequency sweep measurements at concentration above 30 mg/mL, indicating formation of a stable network through "face-to-edge" interaction. (Cummins H Z., Journal of Non-Crystalline Solids. 2007; 353:3891-905).
Figure 1:
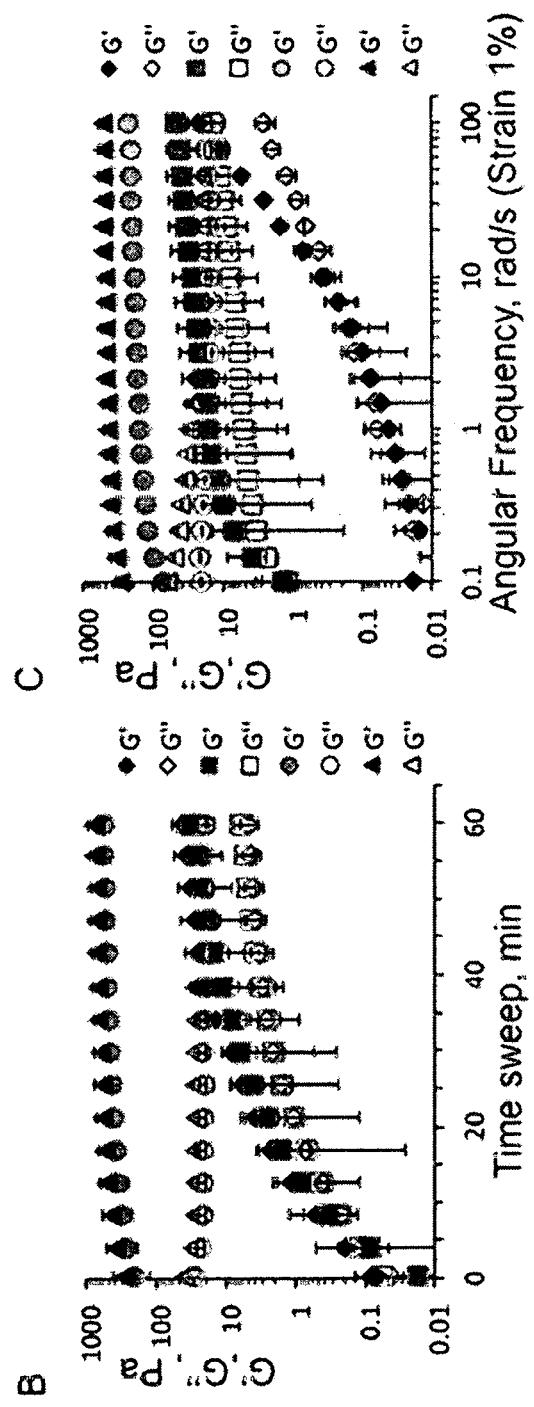

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the term "patient" or "subject" refers to members of the animal kingdom including but not limited to human beings and "mammal" refers to all mammals, including, but not limited to human beings.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

By "biocompatible", it is meant that a device, scaffold composition, etc. is essentially, practically (for its intended use) and/or substantially non-toxic, non-injurious or non-inhibiting or non-inhibitory to cells, tissues, organs, and/or organ systems that would come into contact with the device, scaffold, composition, etc.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer. An "oligomer" is a polymer that comprises a small number of monomers, such as, for example, from 3 to 100 monomer residues. As such, the term "polymer" includes oligomers. The term polypeptide includes polypeptides and oligopeptides.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain linking groups are incorporated into the polymer backbone or are removed in the polymerization process. A polymer is said to comprise a specific type of linkage if that linkage is present in the polymer. An incorporated monomer is a "residue".

A "hydrogel" is a water insoluble, three-dimensional network of polymer chains, and in the context of the present invention, silicate platelets, plus water that fills the voids between the polymer chains. Hydrogels are mostly water (the mass fraction of water is much greater than that of polymer). They do not flow, but they allow small molecules to diffuse, so long as those small molecules do not bind the platelets or polymer. The hydrogels described herein are shear-thinning, meaning that they are non-Newtonian fluids that lose viscosity under shear strain, such as a stirring force, or forces encountered in a medical syringe when the plunger is moved.

In one aspect a shear-thinning composition as described herein is used as a carrier for release of a therapeutic agent e.g., for therapeutic purposes. In one aspect, the therapeutic agent binds to a gelling agent, such as a sulfated or sulfamated polymer or an anionic or cationic composition, such as a polyanionic or polycationic oligopeptide. In one aspect, the therapeutic agent binds specifically or non-specifically to a sulfated or sulfamated polymer. In one example, a therapeutic agent is combined into the shear thinning composition, and the composition is then implanted in a patient or otherwise administered to the patient, for example, by injection or application to a wound or another site in a patient suitable for delivery of the therapeutic agent. The therapeutic agent is added to the other ingredients in the shear-thinning composition by mixture with the gelling agent, such as a sulfated or sulfamated polymer, and the silicate platelets, or by adsorption to or absorption into a gel formed by the gelling agent and the silicate platelets. Generally, the therapeutic agents include any substance that can be mixed with, embedded into, absorbed into, adsorbed to, or otherwise attached to or incorporated onto or into the composition described herein or incorporated into a drug product that would provide a therapeutic benefit to a patient. Non-limiting examples of such therapeutic agents include growth factors, cytokines, chemoattractants, antimicrobial agents, emollients, retinoids, antibodies and fragments thereof, and topical steroids. Each therapeutic agent may be used alone or in combination with other therapeutic agents. For example and without limitation, a composition comprising angiogenic agents may be applied to a wound.

In one aspect, a shear-thinning therapeutic composition is provided. The composition comprises: silicate platelets, a gelling agent, such as a sulfated or sulfamated polymer, non-covalently linking the platelets to form a shear-thinning composition; and a therapeutic agent that non-covalently binds to, specifically or non-specifically, the gelling agent and/or the platelets. For example, the therapeutic agent is non-covalently bound to sulfated or sulfamated polymer complexed non-covalently with the silicate platelets to form a shear-thinning gel.

According to certain aspects, the ratio of therapeutic agent to the gelling agent, such as a sulfated or sulfamated polymer, e.g. heparin, ranges from 1:16000 to 1:1 by weight. In one aspect, the ratio of therapeutic agent to the gelling agent, such as a sulfated or sulfamated polymer, e.g. heparin, ranges from 1:8000 to 1:3. In a further aspect, the ratio of therapeutic agent to the gelling agent, such as a sulfated or sulfamated polymer, e.g. heparin, ranges from 1:1520 up to 1:3 by weight.

According to certain aspects, the ratio of the gelling agent, such as a sulfated or sulfamated polymer, e.g. heparin, to the silicate platelets, e.g. LAPONITE®, ranges from 1:10 to 1:1 by weight. For example, seen below, heparin-LAPONITE® gels are prepared from 1.9+19 mg/mL to 19+19 mg/mL of heparin+LAPONITE®, resulting in rapid gelation. In one aspect, a ratio of sulfated or sulfamated polymer, e.g. heparin to LAPONITE® is 1.9+19 mg/mL to 9.5+19 mg/mL, or a sulfated or sulfamated polymer, e.g. heparin, to LAPONITE® ratio of from 1:10 to 1:2 is used. Such H/L weight ratio is applicable to other combinations of sulfated or sulfamated polymer with LAPONITE®, or other silicate platelet compositions.

In aspects, the LAPONITE® concentration ranges from 10 mg/mL to 80 mg/mL (1% to 8%), and in certain aspects from 15 mg/mL to 50 mg/mL (1.5% to 5.0%).

The above ratios of therapeutic agent to gelling agent, such as a sulfated or sulfamated polymer, e.g. heparin, to silicate platelets are based on studies of FGF2, heparin, and LAPONITE®. These results can be generalized to other therapeutic agents, other gelling agent, such as sulfated or sulfamated polymers, and other silicate platelets.

In the examples below, controlled release is demonstrated by loading 500 ng FGF2 in 525 μL of heparin-LAPONITE® gels to form FGF2-heparin-LAPONITE® gels at 0.00095+ 3.8+19 mg/mL, 0.00095+7.6+19 mg/mL and 0.00095+ 15.2+19 mg/mL. The FGF2 to heparin to LAPONITE® weight ratios in these three formulations are 1:4000:20000, 1:8000:20000 and 1:16000:20000. FGF2-heparin-LAPONITE® gel at 0.00095+7.6+19 mg/mL showed almost 100% release in 34 days. Therefore, in one aspect, a protein to heparin ratio of 1:8000 is selected.

In the in vivo angiogenesis study below, 50 and 500 ng FGF2 was loaded in 100 μL of heparin-LAPONITE® gel to form FGF2-heparin-LAPONITE® gels at 0.0005+7.6+19 mg/mL and 0.005+7.6+19 mg/mL. The subcutaneous implantation with 500 ng FGF2-loaded heparin-LAPONITE® gel showed strong angiogenesis efficacy. Therefore in one aspect, a protein to heparin ratio of 1:1520 used for an in vivo angiogenesis study in a mouse model, and in others aspect a protein to heparin ratio range from 1:1520 to 1:3 by weight is provided.

As used herein, silicate platelets are found naturally in silica clays (natural platelets) or can be manufactured (synthetic platelets). Silicate clays are phyllosilicates (sheet silicates). In nature, the sheets often are microparticles (from 1 to 1000 microns in its largest cross-section) and/or nanoparticles (from 1 to 1000 nanometers in its largest cross-section). Phyllosilicate clay particles are plate-like particles having a perimeter shape that is generally rounded (e.g., circular, elliptical, or oval), polyhedral (e.g., hexagonal), or any closed figure, and are referred to as platelets (see, e.g. FIG. 1A). Platelets have an aspect ratio (the ratio of the largest dimension of the sheets/discs to thickness of the sheet/disk), for example and without limitation, of greater than 50, and more typically ranging from 100 to 1,500. Silicate platelets typically comprise an oxide silicate with alkali metals, alkaline earth metals, and/or hydroxide, optionally including other elements, such as aluminum and iron.

In one aspect, the silicate platelets are LAPONITE®. LAPONITE® (hydrous sodium lithium magnesium silicate) is a synthetic crystalline layered silicate colloid with crystal structure and composition closely resembling the natural smectite clay hectorite. When dispersed in water, LAPONITE® hydrates and swells to form a clear colloidal dispersion with the Na$^+$ ions forming double layers on the faces. The pH for a 2% LAPONITE® suspension in pure water is ~9.8. At low ionic strength, electrostatic repulsion keeps the particles apart. LAPONITE® is decomposed by acids, leading to an increase in ion concentration with time at low pH. At concentrations of 2% or greater in water a gel will form rapidly. LAPONITE® gel is strongly thixotropic, i.e. its viscosity decreases rapidly under shear. After the shear stress is removed, the gel reforms; the rate of restructuring depends on composition, electrolyte level, age of the dispersion, and temperature. The addition of salts reduces the thickness of the electrical double layer, promoting gel formation (Cummins H Z, Liquid, glass, gel: The phases of colloidal LAPONITE®, *Journal of Non-Crystalline Solids* 353 (2007) 3891-3905).

LAPONITE® XLG (Na$^+_{0.7}$[(Si$_7$Mg$_{5.5}$Li$_{0.3}$)O$_{20}$(OH)$_4$]$^-_{0.7}$), a synthetic silicate, is a plate-like nanoparticle with negatively charged surface and positively charged edge (Cummins H Z., Journal of Non-Crystalline Solids. 2007; 353:3891-905). LAPONITE® shows good biocompatibility and biodegrades into non-toxic and bioabsorbable byproducts of Na$^+$, Mg$^{2+}$, Si(OH)$_4$ and Li$^+$ (Gaharwar A K, et al., Bioactive silicate nanoplatelets for osteogenic differentiation of human mesenchymal stem cells. Adv Mater. 2013; 25:3329-36).

Gelling Agent

A gelling agent is used herein to non-covalently bind to or complex with the silicate platelets in the shear-thinning composition.

In one aspect, the gelling agent is a sulfated or sulfamated polymer. In one aspect, the sulfated or sulfamated polymer is a sulfated or sulfamated polysaccharide or oligosaccharide. Synthetic and natural sulfated or sulfamated polysaccharides include oligosaccharides, and further include, for example and without limitation, sulfated glycosaminoglycans or sulfated galactans, ulvans and fucans (See, e.g., Jiao, G., et al. Chemical Structures and Bioactivities of Sulfated Polysaccharides from Marine Algae (2011) *Mar. Drugs* 9:196-223). Non-limiting examples of sulfated or sulfamated polysaccharides include, pentosan polysulfates, dermatan sulfates, keratan sulfates, chondroitin sulfates, sulfated agarans (e.g., porphyrans), and carageenans.

By "sulfated", it is meant that the polymer comprises one or more pendant sulfate (—OSO$_3$) groups. By "sulfamated" it is meant one or more pendant sulfamate (—NSO$_3$) groups. By "sulfated or sulfamated" it is meant a polymer comprises one or more sulfate groups, one or more sulfamate groups, or one or more each of sulfate groups and sulfamate groups. Examples of suitable sulfated or sulfamated polysaccharides include, without limitation: a sulfated polysaccharide, a sulfamated polysaccharides, a sulfated or sulfamated polydisaccharide, a sulfated glycosaminoglycan, heparin, and heparan sulfate (see, e.g., FIG. 2).

In another aspect, the sulfated or sulfamated polymer is a sulfated or sulfamated synthetic polymer, such as a polyurethane, polyester, polyurea, polyamide-ester, polyether, polycarbonate, polyamide, or polyolefin, or copolymers thereof, as are broadly-known in the polymer arts. In another aspect, the sulfated or sulfamated polymer comprises at least one moiety selected from the following:

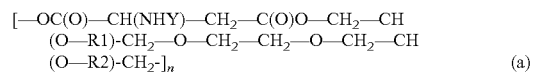

(a)

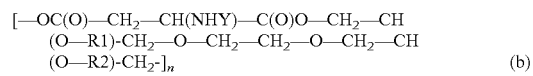

(b)

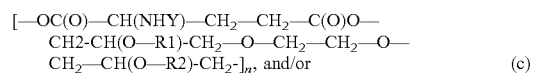

(c)

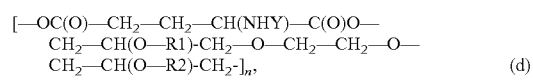

(d)

wherein Y is —C(O)—CH(NH$_3^+$)—(CH$_2$)$_3$—NH—C(NH$_2$)$_2^+$ or —C(O)—CH(NH$_3^+$)—(CH$_2$)$_4$—(NH$_3$)$^+$, n>1, and R1 and R2 are the same or different and are independently selected from the group consisting of sulfate-containing groups and sulfamate-containing groups, with the composition having an overall negative charge. A sulfate-containing group is a moiety (portion of a molecule) comprising at least one pendant sulfate group. A sulfamate-containing group is a moiety (portion of a molecule) comprising at least one pendant sulfamate group.

In other aspects, the gelling agent is a cationic or anionic compound. Cationic and anionic molecules include the water soluble amino acids such as lysine, arginine, glutamic acid, aspartic acid, and hydrophilic amino acids, including glutamine, histidine, asparagine, serine, tyrosine, threonine and other water soluble amino acids; cationic oligo-peptides, such as the dimer, trimer, tetramer, pentamer and hexamer etc. of the above mentioned cationic amino acids, optionally comprising a plurality of the above mentioned cationic amino acids, such as poly(arginine) or poly(lysine); anionic oligo-peptides and polypeptides, e.g., of above mentioned anionic amino acids, optionally comprising a plurality of the above mentioned anionic amino acids, such as poly(glutamic acid) or poly(aspartic acid); and hydrophilic oligopeptides and polypeptides, e.g., of above mentioned hydrophilic amino acids. In one aspect, oligomers of cationic amino acids are from 2 to 10, or optionally from 2 to 6 amino acids. Oligomers or polypeptides of anionic amino acid, or hydrophilic amino acids, or poly (anionic amino acids), or poly(hydrophilic amino acids), or combinations thereof are expected to have no limitation as to the number of amino acids in a peptide sequence.

Gelling agents according to any aspect described herein, may be modified to include biologically active groups or therapeutic agents covalently bound (attached) to the polymer structure in addition to the non-covalent inclusion of a therapeutic agent into the shear-thinning composition.

In preparation of the shear-thinning composition as described herein, a therapeutic agent is admixed with the gelling agent and silicate platelets in any order that allows for formation of a shear-thinning composition. In one aspect, the therapeutic agent is first mixed with the gelling agent, e.g., the sulfated or sulfamated polymer, according to any aspect described herein, and then is mixed with the silicate platelets, according to any aspect described herein, to form a shear-thinning composition, e.g., a hydrogel. Therapeutic agents may be combined in safe and effective amounts. Therapeutic agents that are strongly hydrophobic and/or non-polar might not combine directly to the sulfated or sulfamated polymer, but are expected to do so when combined with a pharmaceutically-acceptable excipient that is charged or otherwise compatible with the system as described herein, or when modified to include hydrophilic or charged groups—so long as the composition retains its pharmacological activity. In one aspect a therapeutic agent, e.g., a hydrophobic therapeutic agent or a therapeutic agent that is not otherwise compatible by itself with the shear thinning composition according to any aspect described herein, is first combined with a cyclodextrin, as are broadly-known in the drug delivery arts.

Salt forms of many of therapeutic agents can be utilized, though the salt counterion may need to be removed to avoid interfering with gelation of the composition described herein. Alternatively, the salt counterion does not need to be removed, but the salt counterion concentration should permit loading and gelling of the composition and formation of a shear-thinning composition. In one aspect, a combination dosage form is provided that is a shear-thinning composition comprising: a gelling agent, e.g. a sulfated or sulfamated polymer, in any aspect described herein; a first therapeutic agent that binds the gelling agent, e.g. the sulfated or sulfamated polymer, for example, where the sulfated or sulfamated polymer is heparin or heparan sulfate, the first therapeutic agent is a member of the heparin interactome; silicate platelets, according to any aspect described herein; and a second therapeutic agent that is any therapeutic agent that does not substantially interfere with formation of the shear-thinning composition. In one aspect, the second therapeutic agent is any therapeutic agent that does not interfere with the formation of a shear-thinning composition, such as a hydrogel. In another aspect, the second therapeutic agent does not bind to the gelling agent, e.g. the sulfated or sulfamated polymer. In yet another aspect, the second therapeutic agent binds specifically to the sulfated or sulfamated polymer. In a further aspect, the sulfated or sulfamated polymer is heparin or heparan sulfate, and the second therapeutic agent is a member of the heparin interactome. Additional therapeutic agents may be combined in the composition, so long as the composition remains shear-thinning.

Therapeutic agents that may be incorporated, by themselves, or in combination with a suitable excipient, into the compositions described herein include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, didofenac, indoprofen sodium salicylamide, antiinflammatory cytokines, and antiinflammatory proteins or steroidal anti-inflammatory agents); antibiotics; anticlotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other therapeutic agents include, without limitation: (1) immunosuppressants; glucocorticoids such as hydrocortisone, betamethasone, dexamethasone, flumethasone, isoflupredone, methylpred-nisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat; (3) antiproliferatives such as sirolimus, paclitaxel, perillyl alcohol, famesyl transferase inhibitors, FPTIII, L744, antiproliferative factor, Van 10/4, 5-FU, Daunomycin, Mitomycin, dexamethasone, azathioprine, chlorambucil, methotrexate, mofetil, vasoactive intestinal polypeptide, and PACAP; (4) antibodies; (5) drugs acting on immunophilins, such as cyclosporine, zotarolimus, everolimus, tacrolimus and sirolimus (rapamycin), interferons, TNF binding proteins; (6) taxanes, such as docetaxel; statins, such as atorvastatin, lovastatin, simvastatin, pravastatin, fluvastatin and rosuvastatin; (7) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, S-Nitroso-N-acetylpenicillamine, S-Nitrosoglutathione, NOC-5, NOC-7, NOC-9, NOC-12, NOC-18, NOR-1, NOR-3, SIN-1, Sodium Nitroprusside, Dihydrate, Spermine NONOate, Streptozotocin; and (8) antibiotics, such as, without limitation: acyclovir, afloxacin, ampicillin, amphotericin B, atovaquone, azithromycin, ciprofloxacin, clarithromycin, clindamycin, clofazimine, dapsone, didazaril, doxycycline, erythromycin, ethambutol, fluconazole, fluoroquinolones, foscamet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, ciprofloxacin, norfloxacin, afloxacin, levofloxacin, gentamicin, tobramycin, neomycin, erythromycin, trimethoprim sulphate, polymixin B and silver salts such as chloride, bromide, iodide and periodate.

Any useful cytokine or chemoattractant can be mixed into, mixed with, or otherwise combined with any composition as described herein. For example and without limitation, useful components include growth factors, interferons, interleukins, chemokines, monokines, hormones, and angiogenic factors. In certain non-limiting aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

Non-limiting examples of angiogenic therapeutic agents include: erythropoietin (EPO), basic fibroblast growth factor (bFGF), acidic fibroblast growth factor (aFGF), fibroblast growth factor-2 (FGF-2), granulocyte colony stimulating factor (G-CSF), granulocyte macrophage colony stimulating factor (GM-CSF), hepatocyte growth factor (HGF), insulin-like growth factors 1 and 2 (IGF-1 and IGF-2), placental growth factor (PIGF), platelet derived growth factor (PDGF), stromal derived factor 1 alpha (SDF-1 alpha), vascular endothelial growth factor (VEGF), angiopoietins (Ang 1 and Ang 2), matrix metalloproteinase (MMP), delta-like ligand 4 (DII4), and class 3 semaphorins (SEMA3s), all of which are broadly-known, and are available from commercial sources.

In certain non-limiting aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acydovir, trifluorouridine, foscamet, penicillin, gentamicin, ganciclovir, iatroconazole, miconazole, Zn-pyrithione, and silver salts such as chloride, bromide, iodide and periodate.

In certain non-limiting aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

Non-limiting examples of antiangiogenic agents include: Macugen (pegaptanib sodium); Lucentis; Tryptophanyl-tRNA synthetase (TrpRS); AdPEDF; VEGF TRAP-EYE; AG-013958; Avastin (bevacizumab); JSM6427; TG100801; ATG3; Perceiva (originally sirolimus or rapamycin); E10030, ARC1905 and colociximab (Ophthotech) and Endostatin. Ranibizumab is currently the standard in the United States for treatment of neovascular AMD. It binds and inhibits all isoforms of VEGF. Although effective in many cases, treatment with ranibizumab requires sustained treatment regimens and frequent intravitreal injections. VEGF Trap is a receptor decoy that targets VEGF with higher affinity than ranibizumab and other currently available anti-VEGF agents. Blocking of VEGF effects by inhibition of the tyrosine kinase cascade downstream from the VEGF receptor also shows promise, and includes such therapies as vatalanib, TG100801, pazopanib, AG013958 and AL39324. Small interfering RNA technology-based therapies have been designed to downregulate the production of VEGF (bevasiranib) or VEGF receptors (AGN211745). Other potential therapies include pigment epithelium-derived factor-based therapies, nicotinic acetylcholine receptor antagonists, integrin antagonists and sirolimus. (See, e.g., Chappelow, A V, et al. Neovascular age-related macular degeneration: potential therapies, *Drugs*. 2008; 68(8):1029-36 and Barakat M R, et al. VEGF inhibitors for the treatment of neovascular age-related macular degeneration, Expert Opin Investig Drugs. 2009 May; 18(5): 637-46.

In another aspect, antioxidants are added to the polymeric composition, such as organic or inorganic antioxidants. In one aspect, the antioxidant is a nanoparticle incorporated by any means into the polymer composition, such as, for example, a cerium nanoparticle. As an example, an anisotropic heart valve or heart valve leaflet prosthesis is manufactured by electrospinning, or by any useful method, and cerium nanoparticles are deposited in and/or on the prosthesis either during or after manufacture.

In one aspect, the therapeutic agent is a member of the interactome of the sulfated or sulfamated polymer that optionally directly binds to, or is a ligand of, the sulfated or sulfamated polymer. By "interactome" (e.g., interaction network) it is meant proteins that interact, however transiently, with a specified composition, and includes both specific and non-specific binding of the therapeutic agent to the sulfated or sulfamated polymer. In one aspect, the member of the specified interactome binds to, and optionally directly binds to the specified composition, e.g. sulfated or sulfamated polymer, and therefore can be characterized as a ligand of the specified composition. The interactomes of various sulfated or sulfamated polymers or oligomers are described in the art. For example, the glycosaminoglycan-protein interaction network is described in Gesslbauer, B., et al. (Exploring the Glycosaminoglycan-Protein Interaction Network by Glycan-Mediated Pull-Down Proteomics, *Electrophoresis* 2016 June; 37(11):1437-47). Ori, A, et al. (A Systems Biology Approach for the Investigation of the Heparin/ Heparan Sulfate Interactome, *J. Biol. Chem*. Jun. 3, 2011; 286(22):19892-19904) describe the heparin/heparan sulfate interactome. For example, Ori, A, et al. describes 442 members of the heparin/heparan sulfate interactome, including, for example and without limitation, the following and cleavage products, recombinant versions, mutated versions, and/or post-translationally modified versions analogs or derivatives thereof that non-covalently bind heparin/heparan sulfate:

4F2 cell-surface antigen heavy chain; 5'-nucleotidase; Alpha-1-antitrypsin; Alpha-1B-glycoprotein; Alpha-2-macroglobulin; Amyloid beta A4 protein; Soluble APP-alpha; Soluble APP-beta; C99; Beta-amyloid protein 42; Beta-amyloid protein 40; C83; P3(42); P3(40); C80; Gamma-secretase C-terminal fragment 59; Gamma-secretase C-terminal fragment 57; Gamma-secretase C-terminal fragment 50; C31; Alpha-1-antichymotrypsin; Angio-associated migratory cell protein; Bile salt export pump; ATP-binding cassette sub-family G member 2; ATP-binding cassette sub-family G member 5; Amiloride-sensitive amine oxidase; Alpha-1B adrenergic receptor; Agouti-related protein; Aminoacyl tRNA synthase complex-interacting multifunctional protein 1; Aldose reductase; Protein AMBP; Inter-alpha-trypsin inhibitor light chain; Trypstatin; Alpha-2-macroglobulin receptor-associated protein; Angiogenin; Angiotensinogen; Angiotensin-2; Angiotensin-3; Antithrombin-III; Annexin A1; Annexin A2; Annexin A3; Annexin A5; Annexin A6; Amyloid-like protein 1; Amyloid-like protein 2; Apolipoprotein A-V; Apolipoprotein B-100; Apolipoprotein E; Beta-2-glycoprotein 1; Aquaporin-1; Arginase-1; Artemin; Agouti-signaling protein; Sodium/potassium-transporting ATPase subunit alpha-1; Sodium/potassium-transporting ATPase subunit beta-1; Sodium/potassium-transporting ATPase subunit beta-3; Plasma membrane calcium-transporting ATPase 1; Copper-transporting ATPase 2; ATP synthase subunit alpha mitochondrial; Attractin; A disintegrin and metalloproteinase with thrombospondin motifs 1; A disintegrin and metalloproteinase with thrombospondin motifs 3; A disintegrin and metalloproteinase with thrombospondin motifs 5; A disintegrin and metalloproteinase with thrombospondin motifs 8; A disintegrin and metalloproteinase with thrombospondin motifs 9; Beta-2-microglobulin; Band 3 anion transport protein; cDNA FLJ57339; Beta-secretase 1; Bone morphogenetic protein 2; Bone morphogenetic protein 3; Bone morphogenetic protein 4; Bone morphogenetic protein 7; Probetacellulin; Complement C1q subcomponent subunit A; Complement C1q subcomponent subunit B; Complement C1q subcomponent subunit C; C4b-binding protein alpha chain; Voltage-dependent L-type calcium channel subunit alpha-1S; Cadherin-8; Azurocidin; Cathepsin B; Cathepsin B heavy chain]; Cathepsin G; Corticosteroid-binding globulin; Carboxypeptidase B2; Carboxypeptidase D; Coiled-coil domain-containing protein 134; Coiled-coil domain-containing protein 80; C-C motif chemokine 1; Eotaxin; C-C motif chemokine 13; C-C motif chemokine 13 medium chain; C-C motif chemokine 13 short chain; C-C motif chemokine 15; CCL15(25-92); CCL15(29-92); C-C motif chemokine 17; C-C motif chemokine 19; C-C motif chemokine 2; C-C motif chemokine 21; C-C motif chemokine 22; MDC(5-69); MDC(7-69)]; C-C motif chemokine 23; CCL23(22-99); CCL23(27-99); CCL23(30-99)]; C-C motif chemokine 24; C-C motif chemokine 25; C-C motif chemokine 27; C-C motif chemokine 28; C-C motif chemokine 3; C-C motif chemokine 4; C-C motif chemokine 5; RANTES; C-C motif chemokine 7; C-C motif chemokine 8; Fibronectin type-III domain-containing protein C4orf31; Antigen-presenting glycoprotein CD1d; Platelet glycoprotein 4; Leukocyte surface antigen CD47; Bile salt-activated lipase; Ceruloplasmin; Uncharacterized protein C6orf15; Complement factor B; Complement factor B Bb fragment; Complement factor D; Complement factor H; Complement factor I; Complement factor I light chain; Chordin; UPF0765 protein C10orf58; Clusterin; Clusterin alpha chain; Chymase; Collagen alpha-1; Collagen alpha-2(I) chain; Complement C2; Complement C2a fragment; Collagen alpha-1(II) chain; Complement C3; Complement C3 alpha chain; C3a anaphylatoxin; Complement C3b alpha' chain; Complement C3c alpha' chain fragment 1; Complement C3dg fragment; Complement C3g fragment; Complement C3d fragment; Complement C3f fragment; Complement C3c alpha' chain fragment 2; Collagen alpha-1(III) chain; Complement C4-A; Complement C4-A alpha chain; C4a anaphylatoxin; C4b-A; C4d-A; Complement C4 gamma chain]; Collagen alpha-1(IV) chain; Collagen alpha-2(IV) chain; Complement C5; Complement C5 alpha chain; C5a anaphylatoxin; Complement C5 alpha' chain; Collagen alpha-1(V) chain; Collagen alpha-3(V) chain; Complement component C6; Collagen alpha-3(VI) chain; Complement C7; Complement component C8 alpha chain; Complement component C8 beta chain; Complement component C8 gamma chain; Complement component C9; Complement component C9b; Collagen alpha-1(IX) chain; Collagen alpha-1(XI) chain; Collagen alpha-2(XI) chain; Collagen alpha-1(XII) chain; Collagen alpha-1(XIII) chain; Collagen alpha-1(XIV) chain; Collagen alpha-1(XVIII) chain; Collagen alpha-1(XIX) chain; Acetylcholinesterase collagenic tail peptide; Cartilage oligomeric matrix protein; Catechol O-methyltransferase; Collagen alpha-1(XXIII) chain; Collagen alpha-1(XXV) chain; Calcium release-activated calcium channel protein 1; Cysteine-rich secretory protein LCCL domain-containing 2; Granulocyte-macrophage colony-stimulating factor; Connective tissue growth factor; Low affinity cationic amino acid transporter 2; Gap junction beta-1 protein; C-X-C motif chemokine 2; C-X-C motif chemokine 6; Small-inducible cytokine B6 N-processed variant 2; Small-inducible cytokine B6 N-processed variant 3]; Platelet basic protein; TC-2; Connective tissue-activating peptide III; Beta-thromboglobulin; Neutrophil-activating peptide 2(74); Neutrophil-activating peptide 2(73); Neutrophil-activating peptide 2; TC-1; Neutrophil-activating peptide 2(1-66); Neutrophil-activating peptide 2(1-63); C-X-C motif chemokine 10; C-X-C motif chemokine 11; C-X-C motif chemokine 13; Cytochrome c; Protein CYR61; Netrin receptor DCC; Estradiol 17-beta-dehydrogenase 11; Estradiol 17-beta-dehydrogenase 12; 17-beta-hydroxysteroid dehydrogenase 13; 3-keto-steroid reductase; Dipeptidyl peptidase 4; Dipeptidyl peptidase 4 soluble form; Endothelin-converting enzyme 1; Extracellular matrix protein 2; Ephrin-A1; Ephrin-A3; Ephrin-A5; Elastin; Neutrophil elastase; Alpha-enolase; Ectonucleotide pyrophosphatase/phosphodiesterase family member 1; Nucleotide pyrophosphatase (NPPase); Ectonucleotide pyrophosphatase/phosphodiesterase family member 3; Nucleotide pyrophosphatase; Receptor tyrosine-protein kinase erbB-2; Coagulation factor X; Factor X heavy chain; Activated factor Xa heavy chain; Coagulation factor XI; Coagulation factor XIa light chain; Coagulation factor XII; Beta-factor XIIa part 1; Beta-factor XIIa part 2; Coagulation factor XIIa light chain]; Protein FAM55A; Coagulation factor IX; Coagulation factor IXa heavy chain; Fibulin-7; Fibrillin-1; Fibrillin-2; Fibrosin-1; IgG receptor FcRn large subunit p51; Fetuin-B; Heparin-binding growth factor 1; Fibroblast growth factor 10; Fibroblast growth factor 12; Fibroblast growth factor 14; Fibroblast growth factor 16; Fibroblast growth factor 17; Fibroblast growth factor 18; Heparin-binding growth factor 2; Fibroblast growth factor 20; Fibroblast growth factor 22; Fibroblast growth factor 3; Fibroblast growth factor 4; Fibroblast growth factor 5; Fibroblast growth factor 6; Keratinocyte growth factor; Fibroblast growth factor 8; Glia-activating factor; Fibroblast growth factor-binding protein 1; Fibroblast growth factor-binding protein 3; Basic fibroblast growth factor receptor 1; Fibroblast growth factor receptor 2; Fibroblast growth factor receptor 3; Fibroblast growth factor receptor 4; Fibrinogen alpha chain; Fibrinogen beta chain; Fibrinogen gamma chain; Fibronectin; UgI-Y1; UgI-Y2; UgI-Y3]; Follistatin; Follistatin-related protein 1; Furin; Protein G6b; Glia-derived nexin; Glial cell line-derived neurotrophic factor; Gelsolin; Growth hormone receptor G-protein coupled receptor 182; Transmembrane glycoprotein NMB; Growth-regulated alpha protein; GRO-alpha(5-73); GRO-alpha(6-73); Solute carrier family 2; facilitated glucose transporter member 2; Proheparin-binding EGF-like growth factor; Hepatoma-derived growth factor; Heparin cofactor 2; Hereditary hemochromatosis protein; Hepatocyte growth factor; Hepatocyte growth factor beta chain; High mobility group protein B1; Haptoglobin; Haptoglobin beta chain; Histidine-rich glycoprotein; Islet amyloid polypeptide; Insulin-like growth factor-binding protein 2; Insulin-like growth factor-binding protein 3; Insulin-like growth factor-binding protein 4; Insulin-like growth factor-binding protein 5; Insulin-like growth factor-binding protein 6; Plasma protease C1 inhibitor; Interferon gamma; Indian hedgehog proteinIndian hedgehog protein C-product; Interferon-inducible GTPase 5; Interleukin-10; Interleukin-12 subunit beta; Interleukin-2; Interleukin-3; Interleukin-4; Interleukin-5; Interleukin-6; Interleukin-7; Interleukin-8; Interleukin-8; IL-8(5-77); IL-8 (6-77); IL-8(7-77); IL-8(8-77); IL-8(9-77); Interphotoreceptor matrix proteoglycan 2; Inhibin beta A chain; Insulin receptor, Insulin receptor subunit beta; Plasma serine protease inhibitor; Integrin alpha-1; Integrin alpha-5; Integrin alpha-5 light chain; Integrin alpha-M; Integrin alpha-V; Integrin alpha-V light chain; Integrin beta-1; Integrin beta-3; Inter-alpha-trypsin inhibitor heavy chain H3; Integral membrane protein 2B; Anosmin-1; Putative keratinocyte growth factor-like protein 1; Putative keratinocyte growth factor-like protein 2; Kininogen-1; T-kinin; Bradykinin; Lysyl-bradykinin; Kininogen-1 light chain; Low molecular weight growth-promoting factor]; Laminin subunit alpha-1; Laminin subunit alpha-2; Laminin subunit alpha-3; Laminin subunit alpha-4; Laminin subunit alpha-5; Laminin subunit gamma-2; Leucyl-cystinyl aminopeptidase; Low-density lipoprotein receptor, Galectin-9; Leucine-rich repeat-containing G-protein coupled receptor 4; Leukemia inhibitory factor receptor; Hepatic triacylglycerol lipase; Endothelial lipase; Lipoprotein lipase; Platelet-activating factor acetylhydrolase IB subunit alpha; Latrophilin-2; Latent-transforming growth factor beta-binding protein 1; L-selectin; P-selectin; Mannose-binding protein C; Multidrug resistance protein 1; Multidrug resistance protein 3; Hepatocyte growth factor receptor; Macrophage migration inhibitory factor Midkine; Matrix metalloproteinase-14; 72 kDa type IV collagenase; Matrilysin); Matrix metalloproteinase-9; 82 kDa matrix metalloproteinase-9; Monocarboxylate transporter 1; Monocarboxylate transporter 8; Multidrug resistance-associated protein 6; Myosin regulatory light polypeptide 9; Neuron navigator 2; Neural cell adhesion molecule 1; Netrin-1; Nicastrin; Noggin; Pro-neuregulin-1; membrane-bound isoform; Neuropilin-1; Neurturin; Sodium/bile acid cotransporter; Occiudin; Zinc finger protein OZF; Calcium-dependent phospholipase A2; Phospholipase A2; membrane associated; Plasminogen activator inhibitor 1; Plasminogen activator inhibitor 1 RNA-binding protein; Proton-coupled folate transporter; Procollagen C-endopeptidase enhancer 2; Proprotein convertase subtilisin/kexin type 5; Proprotein convertase subtilisin/kexin type 6; Programmed cell death protein 5; Platelet-derived growth factor subunit A; Platelet-derived growth factor subunit B; Protein disulfide-isomerase; Protein disulfide-isomerase A6; Phosphatidylethanolamine-binding protein 1; Platelet endothelial cell adhesion molecule; Pigment epithelium-derived factor; Myeloperoxidase; 84 kDa myeloperoxidase; Myeloperoxidase light chain; Myeloperoxidase heavy chain; Platelet factor 4 variant; Platelet factor 4 variant(5-74); Platelet factor 4 variant(6-74)]; Basement membrane-specific heparan sulfate proteoglycan core protein; LG3 peptide; Biglycan; Polymeric immunoglobulin receptor; Putative phospholipase B-like 1; Platelet factor 4; Placenta growth factor; Plasminogen; Activation peptide; Angiostatin; Plasmin heavy chain A short form; Plasmin light chain B; Serum paraoxonase/arylesterase 1; Serum paraoxonase/arylesterase 2; Serum paraoxonase/lactonase 3; Periostin; Peptidyl-prolyl cis-trans isomerase B; Peroxiredoxin-4; Prolargin; Bone marrow proteoglycan; Major prion protein; Prolactin; Vitamin K-dependent protein C; Vitamin K-dependent protein C heavy chain; Activation peptide; Properdin; Presenilin-1; Presenilin-1 CTF subunit; Presenilin-1 CTF12; Protein patched homolog 1; Pleiotrophin; Receptor-type tyrosine-protein phosphatase C; Stromal cell-derived factor 1 gamma; Liver-specific organic anion transporter 3TM13; SLCOIA2 protein; Mannan-binding protein; 60S ribosomal protein L22; 60S ribosomal protein L29; Roundabout homolog 1; R-spondin-1; R-spondin-2; R-spondin-3; R-spondin-4; 40S ribosomal protein SA; Solute carrier family 12 member 9; Sodium-dependent phosphate transporter 2; Solute carrier family 22 member 1; Solute carrier family 22 member 7; Solute carrier family 22 member 18; Sodium-coupled neutral amino acid transporter 3; Sodium-coupled neutral amino acid transporter 4; Zinc transporter ZIP4; Electrogenic sodium bicarbonate cotransporter 1; Serum amyloid A protein; Serum amyloid protein A(2-104); Serum amyloid protein A(3-104); Serum amyloid protein A(2-103); Serum amyloid protein A(2-102); Serum amyloid protein A(4-101)]; Serum amyloid P-component; Sodium channel protein type 5 subunit alpha; Stromal cell-derived factor 1; SDF-1-alpha(3-67)]; Semaphorin-5A; Semaphorin-5B; Secreted frizzled-related protein 1; Sonic hedgehog protein; Sonic hedgehog protein C-product; Beta-galactoside alpha-2,6-sialyltransferase 1; Slit homolog 1 protein; Slit homolog 2 protein; Antileukoproteinase; Synaptogyrin-1; Superoxide dismutase [Cu—Zn]; Extracellular superoxide dismutase [Cu—Zn]; Sortilin; Sderostin; Stabilin-2; EGF-like, laminin-type, EGF-like and link domain-containing scavenger receptor 2; Metalloreductase STEAP4; Stromal interaction molecule 1; Alpha-synuclein; Microtubule-associated protein tau; Teneurin-1; Tenascin; Tenascin-X; Tissue factor pathway inhibitor; Transferrin receptor protein 1, serum form; Transferrin receptor protein 2; Transforming growth factor beta receptor type 3; Transforming growth factor beta-1; Transforming growth factor beta-2; Protein-glutamine gamma-glutamyltransferase 2; Thioredoxin; Prothrombin; Thrombin light chain; Thrombin heavy chain; Thyroglobulin; Metalloproteinase inhibitor 3; T-cell immunomodulatory protein; Tumor necrosis factor ligand superfamily member 13; Tumor necrosis factor, Tumor necrosis factor soluble form; Tissue-type plasminogen activator Tissue-type plasminogen activator chain B; Tumor necrosis factor receptor superfamily member 11B; Serotransferrin; Lactotransferrin; Lactoferroxin-A; Lactoferroxin-B; Lactoferroxin-C; Trypsin-1; Tryptase alpha/beta-1; Tryptase beta-2; Tumor necrosis factor-inducible gene 6 protein; Thrombospondin-1; Thrombospondin-2; Thrombospondin-3; Thrombospondin-4; Transthyretin; Urokinase-type plasminogen activator; Vascular endothelial growth factor A; Vascular endothelial growth factor B; Vascular endothelial growth factor receptor 1; Vascular endothelial growth factor receptor 2; Vitamin D-binding protein (DBP) (VDB) (Gc-globulin) (Group-specific component); Vitronectin; von Willebrand factor Proto-oncogene Wnt-1; Fractalkine; Lymphotactin; Xanthine dehydrogenase/oxidase; Zinc transporter 1 (ZnT-1); and Protein Z-dependent protease inhibitor.

Figure 7:
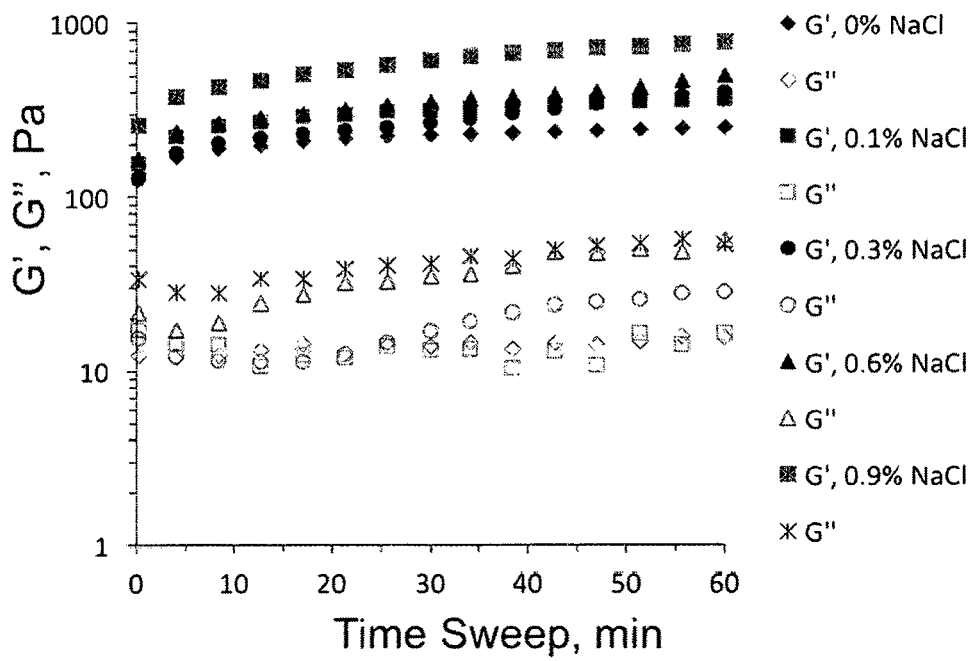
FIG. 7. Oscillatory time sweep measurements of heparin-LAPONITE® gels with H/L ratio fixed at 4:10 (7.6+19 mg/mL) but containing different content of NaCl. (Diamond) 0 wt. %, (Square) 0.1 wt. %, (Circle) 0.3 wt. %, (Triangle) 0.6 wt. % and (Asterisk) 0.9 wt. %. Compare with heparin-LAPONITE® gel without NaCl, the gels containing NaCl ranged from 0.1 to 0.9 wt. % show an increased gelation rate with G' and G" almost tripled as the NaCl content increased from 0 to 0.9 wt. %. This result indicates that heparin together with reasonable amount of salt ions enhanced gelation process, instead of inhibiting or retarding gelation. This is mainly because salt ions promoted LAPONITE® gelation.

Pharmaceutically acceptable salts of any therapeutic agent bound to or otherwise combined with, or incorporated into the shear-thinning composition according to any aspect herein, may be employed. Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts. It should be noted that for inorganic salts, the content to be loaded in this hydrogel may be limited, because addition of salts will promote gelation of the silicate platelets. As such, in certain instances, salt forms may not be used, or counterions should be removed, for example by ion exchange, prior to mixing the therapeutic agent or therapeutic agent plus sulfated or sulfamated polymer with the silicate platelets. However, some salt content, for example as shown in FIG. 7, will actually promote gelation.

As used herein, the terms "drug" and "drugs" refer to any compositions having a preventative or therapeutic effect, including and without limitation, antibiotics, peptides, hormones, organic molecules, vitamins, supplements, factors, proteins and chemoattractants. A "therapeutic agent" (e.g. FGF-2, below) is the pharmacologically-active constituent of a drug product (e.g., the shear thinning composition below comprising LAPONITE®, heparin, and FGF-2, also referred to herein as a therapeutic composition).

According to one aspect of the invention, a method of making a shear-thinning therapeutic composition (a drug product) is provided. The method comprises mixing a sulfated or sulfamated polymer with a therapeutic agent that is a binding partner of the sulfated polymers or oligomers to produce a complex of the sulfated or sulfamated polymer and the therapeutic agent; and mixing the complex of the sulfated or sulfamated polymer and the therapeutic agent with natural or synthetic silicate platelets to produce a shear-thinning hydrogel. According to additional aspects, one or more additional, different, therapeutic agent(s) are combined with the sulfated or sulfamated polymers or oligomers and/or the natural or synthetic silicate platelets prior to or during any mixing step to produce a combined dosage form. Alternatively, the therapeutic agent is first mixed with the silicate platelets and then with the sulfated or sulfamated polymer. In yet another aspect, the therapeutic agent is mixed with the silicate platelets and with the sulfated or sulfamated polymer at the same time.

In use, the shear-thinning composition according to any aspect described herein is administered to a patient. For example, the composition is administered parenterally, e.g. subcutaneously or intramuscularly. In one aspect, the composition is placed into or is distributed in a medical syringe. During delivery, a force is applied, resulting in a loss of viscosity of the composition, and the composition is passed through a needle, cannula, catheter, or any useful tube for delivery of the composition at a site for delivery in a patient, for example and without limitation, within a wound, abdomen or peritoneal cavity of a patient. Small globules of the composition can be placed at any suitable site of the patient, or within a tissue engineering scaffold. In one aspect, the composition is injected or otherwise implanted at a site of a wound or tissue defect in the patient, wherein the composition is used as a soft tissue filler, which can find use in plastic surgery and reconstructive surgery, for example in the case of maxillofacial injury or defect repair, or in breast reconstructive surgery.

In a further aspect, a commercial kit is provided comprising a composition described herein. A kit comprises suitable packaging material and the shear-thinning composition according to any aspect described herein. In one non-limiting aspect, the kit comprises a therapeutic shear-thinning composition according to any aspect described herein in a vessel, which is the packaging, or which is contained within packaging. In various aspects, the vessel is a vial, a medical syringe, tube or any other container suitable for storage and transfer in commercial distribution routes of the kit.

Example 1

A versatile hydrogel for tissue regeneration that preserves the bioactivity of growth factors is tested. The shear-thinning gel self-assembles within one minute from heparin and LAPONITE®. By not covalently modifying heparin, it retains its natural affinity towards many proteins anchored in the extracellular matrix. In principle, Heparin-LAPONITE® gel can bind any heparin-binding compound or composition, e.g., a growth factor. Fibroblast growth factor-2 (FGF2) is used as proof-of-concept. Heparin in the gel protects FGF2 from proteolytic degradation and allows it to be released over time with preserved bioactivity. FGF2 released from subcutaneously injected gel and induces strong angiogenesis in a mouse model. The hydrogel degrades completely in vivo in 8 weeks with or without growth factors, eliciting mild inflammatory response but having little impact on the surrounding tissue. The ease of preparation and scale-up makes this protein delivery platform attractive for clinical translation.

Materials and Methods:

Preparation of Heparin-LAPONITE® Hydrogel (Heparin-LAPONITE®):

LAPONITE® XLG and heparin sodium salt were donated by BYK Additives Inc. (Texas, USA) and Scientific Protein Laboratories, LLC (Waunakee, USA) respectively. All LAPONITE® dispersions were prepared by dispersing LAPONITE® powder in deionized water with vigorously magnetic stirring for 2 h before use. Concentration of heparin solutions ranged from 40 to 400 mg/mL and were prepared by dissolving heparin sodium salt in deionized water. When preparing Heparin-LAPONITE® gels, 0.1 mL of heparin solution was quickly added to 2.0 mL of LAPONITE® dispersion and immediately manually swirled for one minute to yield Heparin-LAPONITE® gel. In this way, 0.1 mL of 40 to 400 mg/mL heparin solutions were separately mixed with 2.0 mL of 20 mg/mL LAPONITE® to yield heparin-LAPONITE® gels comprised of heparin and LAPONITE® with concentrations ranged from 1.9+19 to 19+19 mg/mL, respectively. The weight ratio of heparin to LAPONITE® (H/L) of the as-made Heparin-LAPONITE® gels was ranged from 1:10 to 10:10.

To prepare Heparin-LAPONITE® gels at different solid concentrations with H/L ratio fixed at 4:10, 40 mg of LAPONITE® powder was dispersed in certain volumes of deionized water to obtain LAPONITE® dispersions with concentrations ranged from 15 to 30 mg/mL, respectively. Then each dispersion was mixed with 0.1 mL of 160 mg/mL heparin solution to yield Heparin-LAPONITE® gels with solid concentrations (heparin+LAPONITE®) ranged from 5.8+14.4 to 11.2+28.0 mg/mL. All heparin-LAPONITE® gels were prepared and immediately used for rheological tests.

To prepare heparin-LAPONITE® gels containing different content of NaCl with H/L ratio fixed at 4:10, 0.1 mL of heparin solutions containing NaCl ranged from 2.1 to 18.9 wt. % were dropwisely added to 2.0 mL of 20 mg/mL LAPONITE® dispersion while maintaining manually swirling during addition. The mixtures were immediately transferred for rheological tests. In this way, the Heparin-LAPONITE® gels containing 0.1 to 0.9 wt. % NaCl were prepared to examine the effects of salt ions on the gelation kinetics and gel properties.

Rheological Study:

Dynamic rheological measurements were performed on AR2000ex (TA Instruments, USA). The as-made Heparin-LAPONITE® gels with different H/L ratio or solid concentrations were immediately transferred to a parallel plate (40 mm diameter, gap distance 750 μm) for rheometry test. To prevent evaporation of solvent, a thin layer of mineral oil was applied to the sample edge during test. Oscillatory time sweep measurement was performed to record the gelation behavior versus time at 37° C. under a controlled strain of 1% and a frequency of 1 rad s$^{-1}$. To investigate viscoelastic properties, angular frequency sweep measurement was conducted to record both storage (G') and loss (G") moduli with angular frequency setup from 0.1 to 100 rad s$^{-1}$ and a strain at 1%. Furthermore, a steady shear rate sweep was performed to investigate the shear thinning behavior of the hydrogels as a function of shear rate from 0.01 to 10 s$^{-1}$. Each sample was replicated at least three times.

Zeta Potential Test:

Zeta potential measurements were performed using zetasizer (Nano-ZS90, Malvern). The LAPONITE® dispersion was diluted to 10 mg/mL and heparin solutions were prepared with concentrations ranging from 20 to 160 mg/mL for use. Then 0.1 mL of 20 to 160 mg/mL heparin solutions was separately mixed with 2.0 mL of 10 mg/mL LAPONITE® dispersion to yield a series of Heparin-LAPONITE® complex suspensions. These Heparin-LAPONITE® complex suspensions were comprised of heparin and LAPONITE® with concentrations between 0.95+9.5 to 7.6+9.5 mg/mL (H/L, 1:10 to 8:10). The Heparin-LAPONITE® complexes were prepared under this condition to avoid gelation, so that the mobility of the conductive components would not be hindered for zeta potential measurements. The H/L ratio of the Heparin-LAPONITE® complexes was remained same to the Heparin-LAPONITE® gels. A LAPONITE® dispersion at 9.5 mg/mL and a series of heparin solutions with concentrations between 0.95 to 7.6 mg/mL were also prepared for comparison. The freshly made Heparin-LAPONITE® complex suspensions, LAPONITE® dispersion and heparin solutions were immediately transferred into a cuvette for zeta potential measurements. At least three readings of each measurement were recorded to calculate the mean value and its standard deviation.

Controlled Release Study:

For in vitro and in vivo studies, all LAPONITE® dispersion and heparin in deionized water solutions were sterilized by filtering through 0.2 μm syringe filter before use. 500 ng FGF2 was loaded in Heparin-LAPONITE® gels with different heparin to LAPONITE® ratio (H/L) for controlled release study. Specifically, 2 μL of 250 ng/μL FGF2 solution was separately mixed with 25 μL of 80, 160 and 320 mg/mL heparin solutions to yield three heparin-FGF2 complexes. The three heparin-FGF2 complexes were then separately added to 500 μL of 20 mg/mL LAPONITE® dispersion in each Eppendorf tube and manually swirled for 1 min to yield three 500 ng FGF2-loaded Heparin-LAPONITE® gels. The three Heparin-LAPONITE® gels were comprised of heparin and LAPONITE® with concentrations of 3.8+19, 7.6+19 and 15.2+19 mg/mL (H/L ratio, 1:5, 2:5 and 4:5) to examine the H/L ratio effects on the FGF2 release kinetics. The FGF2-loaded Heparin-LAPONITE® gels were centrifuged at 5000 rpm for 15 second to remove air bubbles and then 200 μL of 0.9% NaCl saline solution was added to the gel top. The controlled release was set up at 37° C. in an incubator for 34 days. At each scheduled time point, the gel tubes were centrifuged at 5000 rpm for 15 second and the supernatant was collected using pipette, and then 200 μL of fresh saline was added for next time point. Such procedure was repeated until the controlled release experiment was completed. The controlled release was replicated three times.

500 ng FGF2 was directly loaded in two LAPONITE® gels with concentration at 22.8 and 26.6 as controls to compare the release behavior from Heparin-LAPONITE® gels. 2 μL of 250 ng/μL FGF2 solution was mixed with 25 μL deionized water and then respectively added to 500 μL of 24 and 28 mg/mL LAPONITE® dispersions and manually swirled for 1 min. The FGF2-loaded LAPONITE® dispersions were incubated at 37° C. for about 2 h to yield two LAPONITE® gels containing 500 ng FGF2 in each gel. All other procedure is same with FGF2-loaded Heparin-LAPONITE® gels for controlled release study. The concentrations of all the released FGF2 samples were determined using ELISA assay kit according to the manufacturer's instruction (PEPROTECH, NJ, USA).

Western Blot Assay:

To insure enough amount of the released FGF2 for Western blot test, 5 μg FGF2 was loaded in Heparin-LAPONITE®, hyaluronic acid-LAPONITE® (HA-LAPONITE®) gels and LAPONITE® control, respectively. Specifically, 5 μL of 1 μg/μL FGF2 was mixed with 25 μL of 160 mg/mL heparin solution and then added to 500 μL of 20 mg/mL LAPONITE® dispersion with manually swirling for 1 min to yield 5 μg FGF2-loaded Heparin-LAPONITE® gel. Same amount of free FGF2 solution was diluted with 25 μL of deionized water and then directly mixed with 500 μL of 20 mg/mL LAPONITE® dispersion to yield 5 μg FGF2-loaded LAPONITE® gel as a control.

HA-LAPONITE® gel was also prepared using a reported protocol (Divya Bhatnagar D X, Dilip Gersappe, and Miriam H. Rafailovich. Hyaluronic Acid and Gelatin Clay Composite. Journal of Chemical and Biological Interfaces. 2014; 2:1-11) for controlled release of FGF2 to compare with our Heparin-LAPONITE® gel. 5 μL of 1 μg/μL FGF2 solution was mixed with 100 μL of 5 mg/mL hyaluronic acid and then added to 500 μL of 30 mg/mL LAPONITE® dispersion with manually swirling for 1 min to yield 5 μg FGF2-loaded HA-LAPONITE® gel.

All FGF2-loaded hydrogels were centrifuged at 5000 rpm for 15 second to remove any air bubbles and 500 μL fresh saline solution was added to each gel top. The controlled release was set up at 37° C. in an incubator for 134 h. The gel tubes were centrifuged at 5000 rpm for 15 second and the supernatants were collected. The concentrations of the released FGF2 were determined by ELISA assay to be 490 ng/mL for Heparin-LAPONITE® gel, and ca. 9.0 and 9.6 ng/mL for both LAPONITE® control and HA-LAPONITE® gel.

According to the released FGF2 concentration, free FGF2 solution at 490 ng/mL and heparin-FGF2 complex solution at 3.9 mg/mL+490 ng/mL were prepared as controls. Then 100 μL of the released FGF2 solution, free FGF2 and heparin-FGF2 complex were separately mixed with 9.8 μg trypsin (FGF2:trypsin=1:200 by wt.) and incubated at 37° C. for 0.5 and 2 h, respectively. The digested solutions were immediately mixed with 100 μL of tricine sample buffer (Bio-Rad Laboratories, CA, USA) and denatured at 100° C. for 5 min. Similarly, FGF2 solutions released from LAPONITE® and HA-LAPONITE® gels were similarly treated with trypsin and denatured with the tricine sample buffer using same procedure.

Western blotting was used to examine the amount of intact FGF2. SDS-PAGE was utilized for separation followed by protein blotting on a PVDF membrane (Bio-Rad Laboratories, Hercules, Calif.). The membrane was blocked with 5% BSA in TBS with 0.05% Tween 20 for 1 h, then incubated with a rabbit anti-human FGF2 polyclonal antibody (1:1,000, Abcam, Cambridge, Mass.). The membranes were washed with TBS 3 times and incubated with a peroxidase conjugated anti-rabbit IgG antibody for 2 h at room temperature. Signals were visualized using the ChemiDic™ XRS+Imaging System (Bio-Rad Laboratories, Hercules, Calif.), and band densities were quantified using NIH ImageJ software.

In Vivo Biocompatibility and Biodegradation:

Male BALB/cJ mice (Jackson Laboratory) with an average age of 8-9 wk were used and cared for in compliance with a protocol approved by the Institutional Animal Care and Use Committee of the University of Pittsburgh. Under isoflurane anesthesia, 100 μL of Heparin-LAPONITE® gel (7.6+19 mg/mL) or LAPONITE® gel (19 mg/mL) was injected in the left back of the mice through a 31G insulin needle. The right back, which did not receive injection, served as the contralateral control. All groups contained four to eight mice. The animals were sacrificed at post-injection day 3, weeks 2, 4, 6 and 8. The subcutaneous tissues were harvested at the injection site and the contralateral site. Tissues were fixed in 10% formalin for 15 min, and then soaked in 30% sucrose and embedded in the Tissue-Tek optimum cutting temperature (O.C.T) compound (Sakura Finetek USA). Cross sections (6-μm thick, longitudinal axial cut) were stained with hematoxylin and eosin (H & E), and Masson's trichrome stain (MTS) and ED-1 to examine inflammation or any adverse effects. For ED-1 immunohistochemical analysis, 6-μm thick sections of the tissues were dried and fixed in histology-grade absolute ethanol for 15 min, air dried, and incubated with rat monoclonal anti-CD68 (1:200, Abcam, Cambridge, Mass.) for ED-1 identification. The slides were then incubated with a goat anti-rat-Alexa 594 (1:400, Life technologies, Carlsbad, Calif.) for 1 hour. ED-1 stained sections were analyzed for the density of newly recruited macrophages. Five to ten 200× magnification images were obtained for each specimen. The image was taken using an inverted microscope Eclipse Ti (Nikon, Melville, N.Y.) equipped with a digital camera (QImaging, BC, Canada).

Angiogenesis Study:

100 μL of Heparin-LAPONITE® gel with or without loading growth factor FGF2 (500 ng) (Peprotech, Rocky Hill, N.J.) was injected in the left back of the mice through a 31G insulin needle. The subcutaneous tissues were harvested on day 3, weeks 2 and 4 post-injection and embedded and frozen in Tissue-Tek OCT compound. Sections of 6-μm thickness were prepared with a cryomicrotome. The following antibodies were applied per supplier instructions: rat anti-mouse CD31 monoclonal antibody (BD Biosciences), a goat anti-rat-Alexa 594, FITC-conjugated anti-α-SMA monoclonal antibody (Sigma). All slides were counterstained with DAPI (Invitrogen). The fluorescent images were taken by a Nikon inverted microscope Eclipse Ti. Six low magnification (100×) fields containing the highest number of CD31– or α-SMA-positive cells were randomly selected for each group. The number of blood vessels in the field was counted and confirmed by DAPI-positive nuclei. The value was divided by the area of the imaged tissue to obtain blood vessel number per unit area and a mean value was calculated based on the six images per group.

Statistical Analysis:

The data of macrophage number and blood vessel number per square millimeter were analyzed using one-way ANOVA statistical analysis with post-hoc Bonferroni correction. A p value<0.05 is considered significant. Data represent mean±standard deviation (SD).

Results and Discussion

Figure 3:
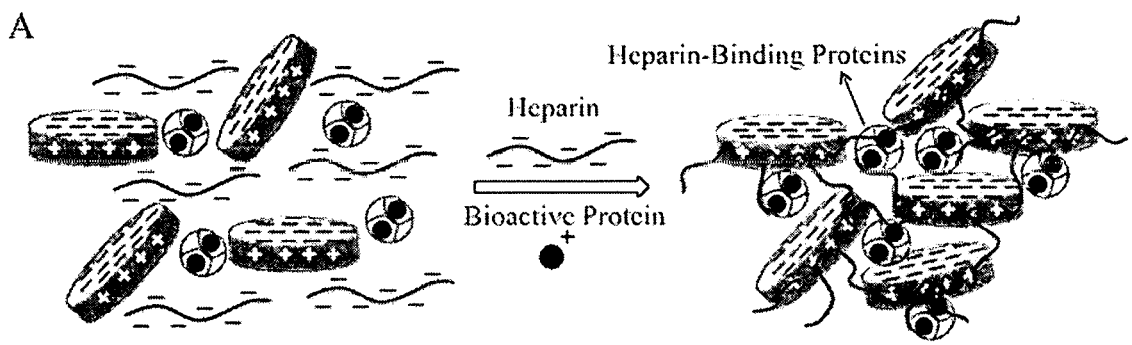
FIG. 3. (A) Schematic illustration of gelation between heparin-protein complex and LAPONITE® to form Heparin-LAPONITE® gel within one minute for sustained release. (B) Oscillatory time sweep and (C) angular frequency sweep measurements of Heparin-LAPONITE® gels. The gels are comprised of LAPONITE® at 19 mg/mL with various heparin concentrations (H/L ratio). (Diamond) 1.9 mg/mL (1:10), (Square) 3.8 mg/mL (2:10), (Circle) 7.6 mg/mL (4:10), (Triangle) 15.2 mg/mL (8:10). (D) Moduli change as a function of heparin concentrations. Heparin quickly gels with LAPONITE® dispersion to form Heparin-LAPONITE® gel upon mixing them at appropriate ratio. At a fixed LAPONITE® concentration, the gelation rate is proportional to heparin concentration. The G' over G" throughout frequency sweep indicates a stable network structure based on rapid reversible crosslinks, which are not disrupted under suitable shear stress. (E) Viscosity change of Heparin-LAPONITE® gels with different solid concentrations as a function of shear rate. All the gels show shear thinning properties, indicating injectability.
Figure 3:
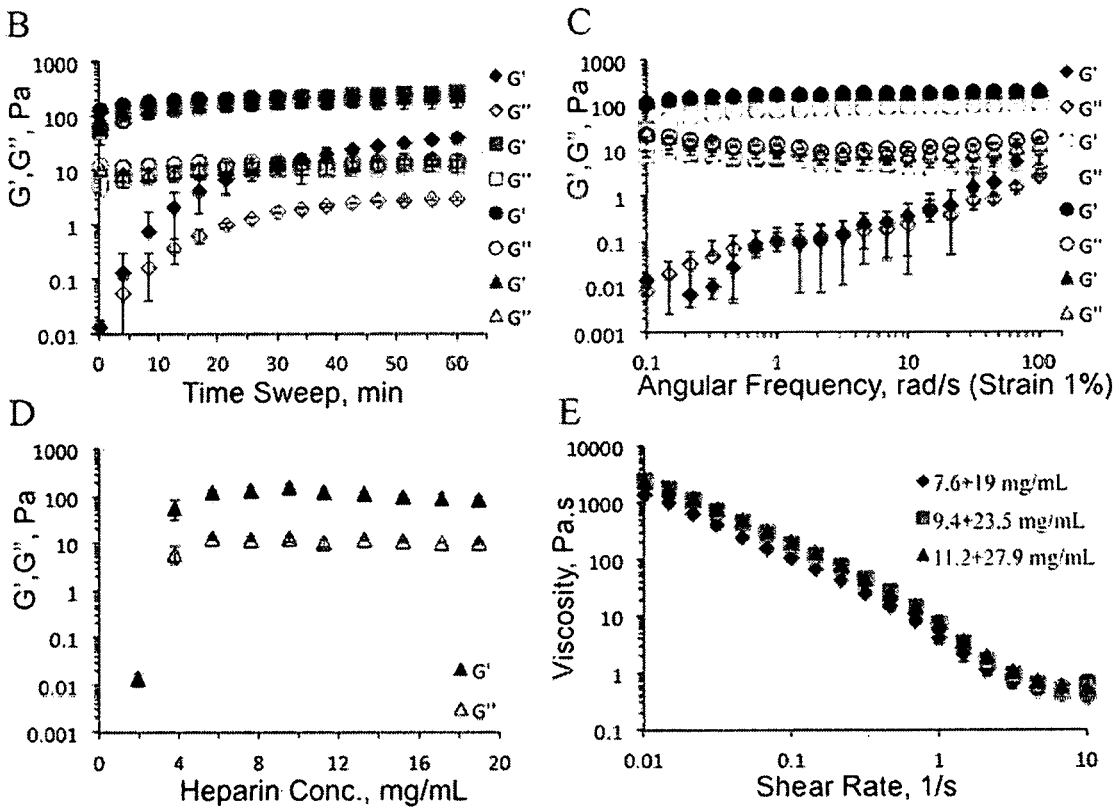
Figure 9:
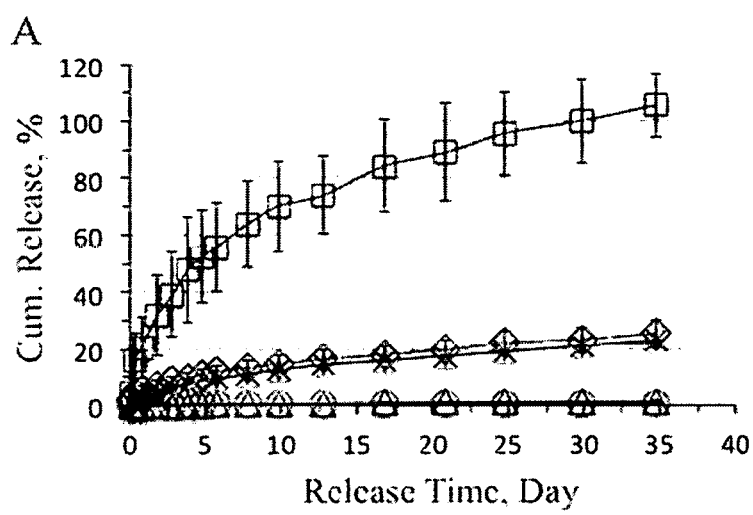
FIG. 9. (A) Cumulative release of FGF2 from heparin-LAPONITE® gels: (Diamond) 3.8+19 mg/mL, (Square) 7.6+19 mg/mL and (Asterisk) 15.2+19 mg/mL; LAPONITE® controls: (Circle) 22.8 mg/mL and (Triangle) 26.6 mg/mL. The FGF2 is sustainably released from heparin-LAPONITE® gels over 34 days with release rate related to the H/L ratio, but a negligible FGF2 is released from both LAPONITE® controls. (B, C) Western blot assays to examine the stability of the released FGF2 from heparin-LAPONITE®, LAPONITE® and hyaluronic acid-LAPONITE® (HA-LAPONITE®) gels with regard to proteolytic degradation. The released FGF2 solution is mixed with trypsin (mass ratio, 1:200) and incubated at 37° C. for 0.5 and 2 h. The FGF2 from heparin-LAPONITE® gel shows a similar band intensity compared to heparin-FGF2 complex control, indicating a heparin-binding FGF2 released from heparin-LAPONITE® gel and protection from protease degradation. The free FGF2 is readily degraded by trypsin treatment within 0.5 h. Neither LAPONITE® nor HA-LAPONITE® gels yield detectable and stable FGF2 before and after treatment with trypsin.
Figure 9:
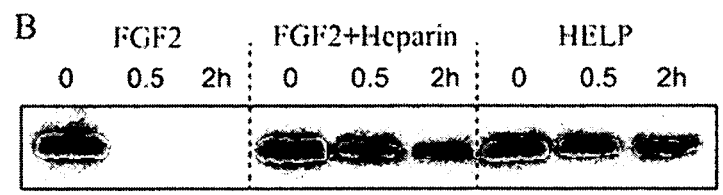
Figure 9:
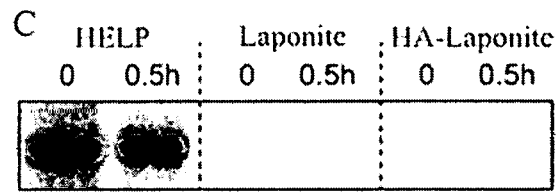

Rapid Gelation Between Heparin and LAPONITE®:

Heparin-LAPONITE® gel is designed for protein delivery by mixing heparin-protein complex solution with LAPONITE® dispersion and manually swirled to gel within one minute (FIG. 3A). To examine the gelation rate between the components, 20 mg/mL of LAPONITE® dispersion was selected to mix with heparin solution to yield Heparin-LAPONITE® gel with H/L ratio ranged from 1:10 to 10:10 (1.9+19 mg/mL to 19+19 mg/mL). The as-made LAPONITE® dispersion itself at this concentration cannot form a weak gel through face-to-edge interaction within about 69 h (Table 1). Dynamic rheological measurements on gelation kinetics, viscoelastic properties revealed the shear thinning behavior of the Heparin-LAPONITE® gel. Oscillatory time sweep measurements indicate that the storage (G') and loss (G") moduli are proportional to the heparin content when the LAPONITE® concentration is fixed at 19 mg/mL (FIG. 3B). The first data points of the measured G' and G" from time sweep measurements were plotted as a function of heparin concentration to evaluate the gelation rate upon mixing the two components (FIG. 3D). It clearly shows that the G' and G" values quickly increase from approximately 0.01 to 120 Pa and 0 to 10 Pa respectively when heparin concentration increases from 1.9 to 5.7 mg/mL (H/L, 1:10 to 3:10), followed by a slow elevation to 150 and 12 Pa at heparin concentration of 9.5 mg/mL (H/L, 5:10). While further increasing heparin content leads to gradually reduced G' and G" again (FIG. 3D, 9.5 to 19 mg/mL). Angular frequency sweep measurements demonstrate that the Heparin-LAPONITE® gels all have stable G' values approximately 7-16 times higher than G" values throughout the frequency sweep from 0.1 to 100 rad s$^{-1}$ except the sample formed at low H/L ratio of 1:10 (FIG. 3C). These results indicate that the heparin and LAPONITE® can quickly form a stable network structure within the appropriate H/L ratio range (as above, in one aspect, a useful H/L weight ratio range is between 1:10 to 1:1 with a LAPONITE® concentration between 10 to 80 mg/mL, and optionally between 15-50 mg/mL, and in this example, 20 mg/mL LAPONITE® was chosen to examine the quick gelation for H/L ratio ranged from 1:10 to 1:1 by weight). The viscosity of LAPONITE® dispersion was highly related to stirring time in deionized water (exfoliating degree). 50 mg/mL LAPONITE® mixed with heparin was used to form a gel and it could be taken into syringe for injection before it became solid-like gel. Generally, below 35 mg/mL LAPONITE® is dispersed in deionized water with vigorous stirring for more than 2 h for use; while above 35 mg/mL, it can be stirred for a short time for use, e.g., about 10-60 min according to its concentration. Such network shows more elastic than viscous properties, which is not disrupted under suitable shear stress due to the rapid reversible interactions. A shear rate sweep measurement was performed to confirm the shear thinning behavior of the gel for injectability (FIG. 3E). Based on these investigations, we speculate that the rapid gelation and stable gel properties can be attributed to several aspects: (1) the negatively charged heparin can diffuse into the LAPONITE® dispersion without microscopic aggregation; (2) the electrostatic interactions between the two components form quickly and thus establish reversible ionic crosslinks rapidly; and (3) the stable LAPONITE® dispersion with uniform particle size facilitates uniform gelation.

TABLE 1

Gelation time of LAPONITE ® dispersion at different concentration.

| | LAPONITE ®, mg/mL | | | |
|---|---|---|---|---|
| | 20 | 26.6 | 32.9 | 39.1 |
| Gelation time* | 69 h | 20 min | 7 min | 1 min |

*The LAPONITE ® dispersions were prepared and then settled for gelation. Gelation time was recorded by inverting each vial for at least 30 seconds without observing any flowable gel.

Figure 2:
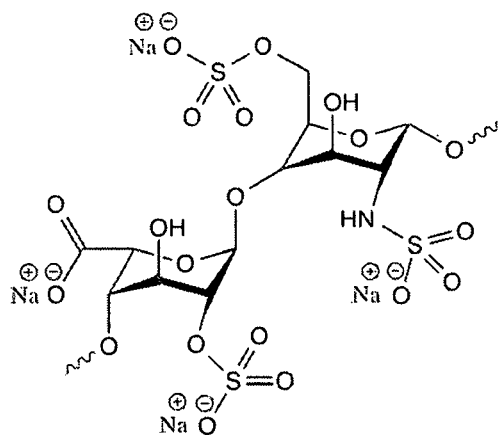
FIG. 2. Chemical structure of heparin sodium salt. The number average molecular weight (Mn) of the heparin used is ca. 20 kDa. Each repeat unit bears four negative charges and approximately 117 negative charges carry on each chain.

The LAPONITE® nanoplatelet carries approximately 1000 negative charges per particle and the particle edge is positively charged which counters approximately 10% of the total negative charges, the rest of the negative charges are balanced by metal ions. The heparin used here has number average molecular weight of ~20 kDa and each chain bears approximately 117 negative charges, though it is believed that a large molecular weight range for heparin or heparan sulfate would be useful (FIG. 2). Owing to such high negative charge density, when suitable amount of the heparin solution is added to LAPONITE® dispersion, heparin molecules can easily diffuse between the nanoplatelets under only gentle swirling for a minute with no need of mechanical stirring to form homogenous mixture. It is theorized that most of the heparin chains are quickly anchored onto LAPONITE® edges, forming effective crosslinks via electrostatic interactions, instead of absorbing on LAPONITE® surfaces due to the strong negative charge repulsion (FIG. 3A). Because of the limited heparin chain length and contact areas between the particle edges, it is likely that only some of the anchored heparin can bridge the adjacent LAPONITE® edges to establish effective crosslinks. This is why the rheometry measurements show that the starting G' upon mixing depends highly on heparin content (FIG. 3D, 1.9 to 5.7 mg/mL). Then a slow elevation to the maximal G' value at 9.5 mg/mL (H/L, 5:10) indicates that an optimal H/L ratio is reached for quickest gelation. In the following region (9.5 to 19 mg/mL), though more free heparins exist in the system, it is estimated that most of them are just anchored onto LAPONITE® edges as pendent chains with little contribution to crosslinking. It appears that the LAPONITE® edges are gradually masked by absorbing more free heparin molecules when the heparin concentration exceeds 9.5 mg/mL, leading to a reduction of the areas for bridging by the anchored chains thus hindering the gelation process. Such phenomenon was observed in PEO gelling with LAPONITE®(Mongondry P, et al. Influence of pyrophosphate or polyethylene oxide on the aggregation and gelation of aqueous LAPONITE® dispersions. Journal of colloid and interface science. 2004; 275:191-6).

Figure 4:
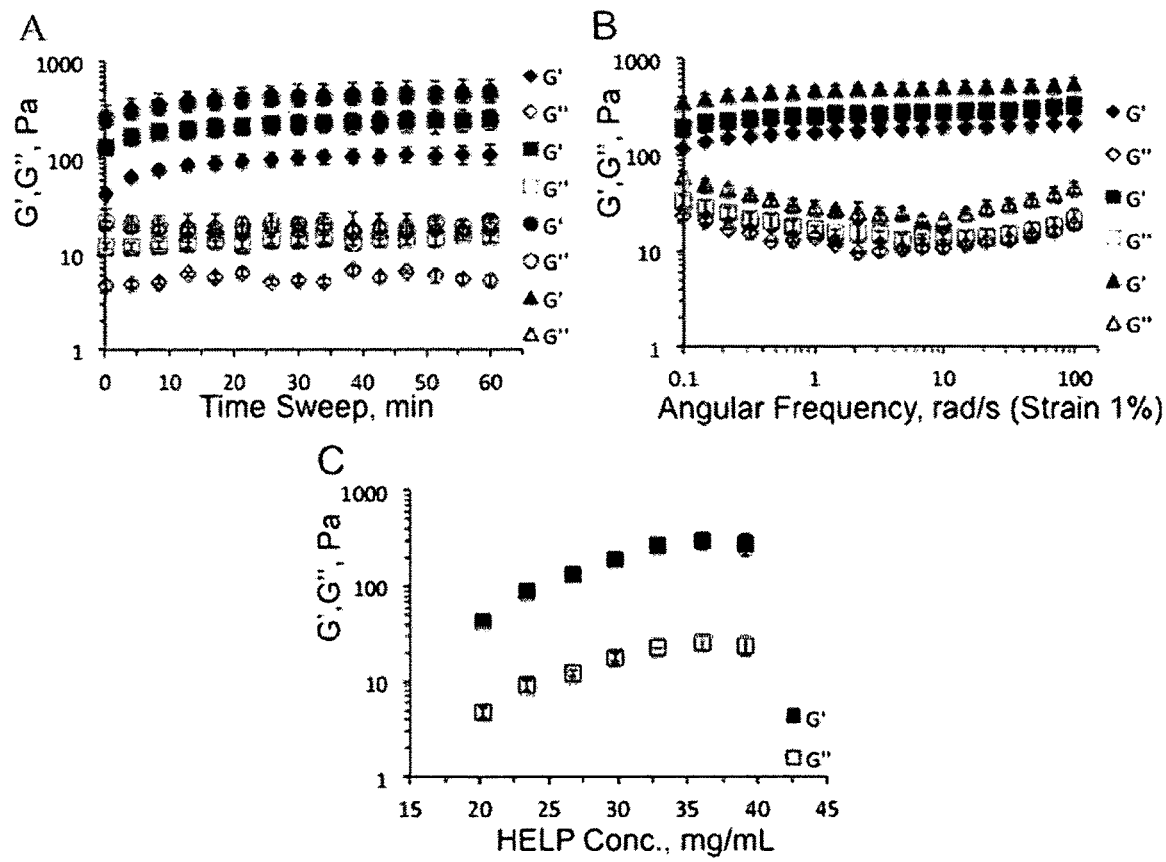
FIG. 4. (A) Oscillatory time sweep measurements of Heparin-LAPONITE® gels at different solid concentrations (heparin+LAPONITE®) with H/L ratio fixed at 4:10. (Diamond) 5.8+14.4 mg/mL, (Square) 7.6+19 mg/mL, (Circle) 9.4+23.5 mg/mL and (Triangle) 11.2+28 mg/mL. (B) The viscoelastic properties of Heparin-LAPONITE® gels at different solid concentrations as a function of angular frequency. (Diamond) 7.6+19 mg/mL, (Square) 9.4+23.5 mg/mL, and (Triangle) 11.2+28 mg/mL. (C) The first data points of G' and G" from time sweep measurements are plotted versus the solid concentrations to evaluate the gelation rate. The moduli are increased steadily as the solid concentration increases with G' approximately 6-19 times higher than that of G", indicating more crosslinks formed at higher solid concentrations. But it reaches maximal G' and G" at 36.1 mg/mL (10.3+25.8 mg/mL), implying that too high solid concentration likely hinders heparin diffusion into the LAPONITE® dispersion and reduce gelation rate.

It is expected that the gelation rate is proportional to LAPONITE® concentration because the spaces between the particles are reduced at higher concentration and thus the anchored heparins can more effectively reach the adjacent particles to form crosslinks. This is consistent with oscillatory rheological measurements of Heparin-LAPONITE® gels as a function of the concentration with the H/L ratio fixed at 2:5 (FIG. 4). It shows that both G' and G" are proportional to the concentrations, but the maximal modulus is reached at 36.1 mg/mL, indicating that excessively high concentration of LAPONITE® likely hinders heparin diffusion and retard gelation. Here, the H/L weight ratio is fixed at 2:5. Namely the gel is comprised of 10.3 mg/mL heparin+ 25.8 mg/mL LAPONITE®. In this case, the LAPONITE® concentration is ranged from 15 mg/mL to 30 mg/mL, which is mixed with heparin at fixed ratio of 2:5 (H/L ratio) to test their viscoelastic properties versus LAPONITE® concentrations. In all the range from 15 mg/mL to 50 mg/mL, heparin can quickly complex with LAPONITE® to form gel with H/L weight ratio ranged between 1:10 to 1:1.

Figure 5:
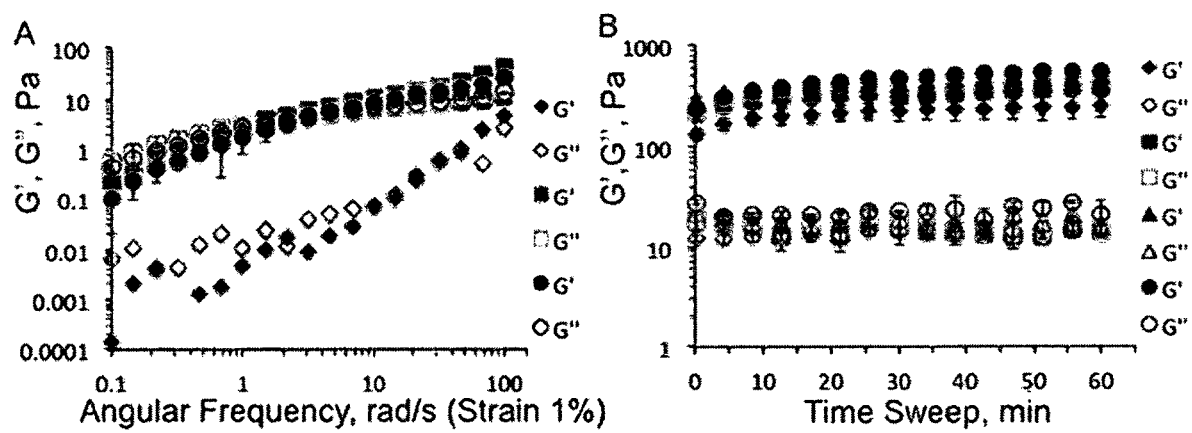
FIG. 5. (A) Angular frequency sweep measurements of LAPONITE® dispersion at 20 mg/mL with different settling time. (Diamond) Fresh dispersion, (Square) 7 days and (Circle) 20 days. The as-made LAPONITE® dispersion at 20 mg/mL only forms a weak gel after mature gelation, which is able to convert into low-viscosity dispersion again after being manually shaken for ca. 2 min. (B) Oscillatory time sweep measurements of the settled LAPONITE® dispersion gelled with heparin solution to form heparin-LAPONITE® gels. Settling time: (Diamond) Fresh dispersion, (Square) 20 days, (Triangle) 40 days and (Circle) 180 days. The LAPONITE® dispersion was settled for up to 180 days, which was manually shaken to convert into low-viscosity dispersion again and then mixed with the heparin solution to form heparin-LAPONITE® gels in a nearly similar manner like the fresh dispersion. The H/L ratio of heparin-LAPONITE® gels was fixed at 4:10 (7.6+19 mg/mL). The results show that the settled LAPONITE® dispersion does not sacrifice any gelation ability with heparin. Frequency sweep measurements show a slightly higher G' and G" than that gelled with the fresh dispersion, indicating that the LAPONITE® dispersion can be stably stocked for at least 6 months and used to gel with heparin. The higher moduli from the settled LAPONITE® dispersion gelled with heparin is likely attributed to the self-organization of the settled LAPONITE® particles, which is easier to be connected by heparin chains when mixing the two components.
Figure 6:
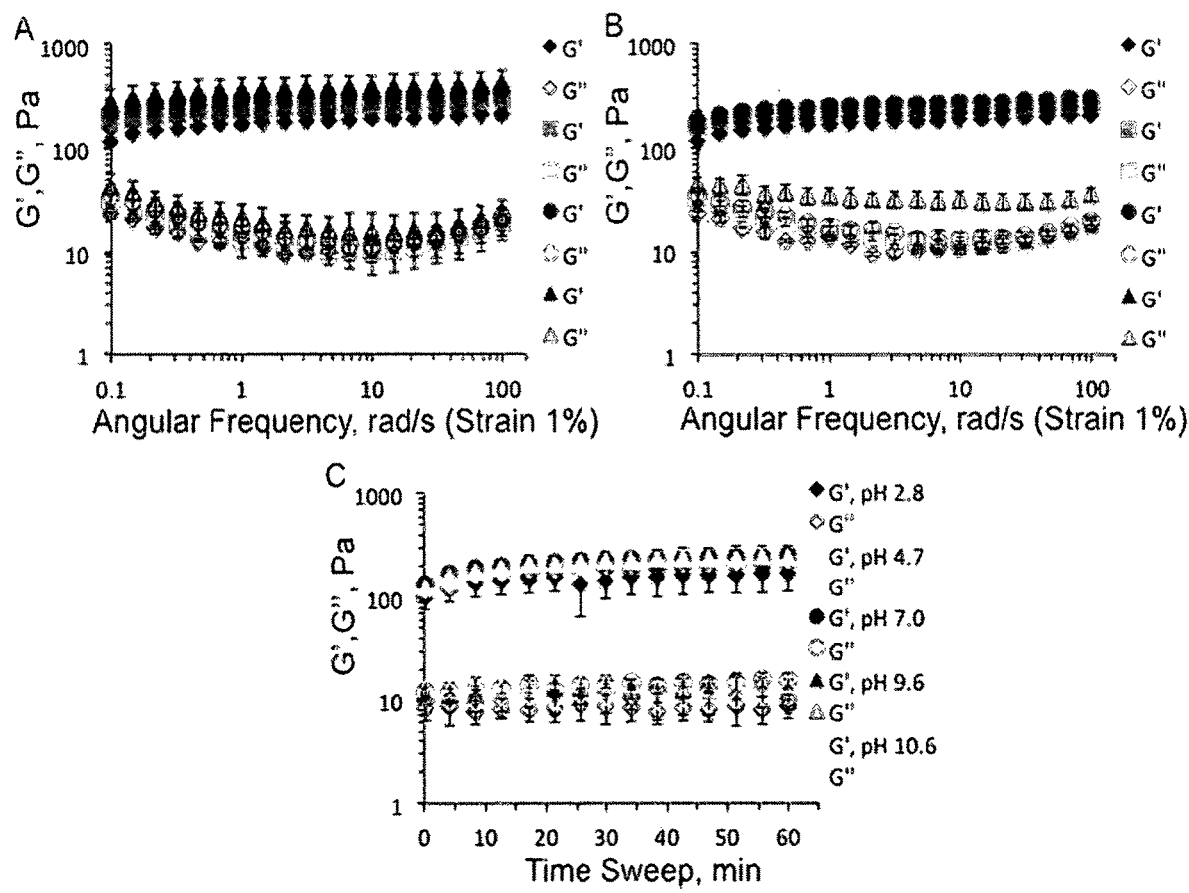
FIG. 6. Comparison of the viscoelastic properties of heparin-LAPONITE® gels after incubating with biological solutions for a different time period. (A) 0.9% NaCl biological saline, and (B) cell medium (EBM-2). (Diamond) No incubation, (Square) 10 min, (Circle) 40 min and (Triangle) 18 h. The freshly made heparin-LAPONITE® gel with H/L ratio at 4:10 (7.6+19 mg/mL) was incubated in biological solutions. The viscoelasticity of all the gels were then examined by angular frequency sweep measurements. Compare with the fresh heparin-LAPONITE® gel, incubation with biological saline or cell medium shows little impacts on the viscoelastic properties under different incubation time, indicating a stable network structure resistant to the interference of ions and other biological components. (C) Time sweep measurements of heparin gelled with LAPONITE® dispersions prepared at different pH levels. The LAPONITE® dispersions were prepared by dispersing in deionized water with pH ranged from 2.8 to 10.6 adjusted by 0.1 M HCl and 0.1 M NaOH solutions. The dispersions were then separately mixed with heparin solutions at H/L ratio at 4:10 by manually swirling for 1 min and then immediately transferred for rheometry test. Time sweep measurements show similar gelation kinetics and viscoelasticity at different pH levels, indicating little effects on gelation caused by the tested pH conditions.

LAPONITE® dispersion at 20 mg/mL is stable for at least 6 months and only forms weak "house-of-cards" gel after mature gelation (FIG. 5A). The weak gel can be easily converted into low-viscosity dispersion by vigorously shaking for approximately 2 minutes, which can then be re-gelled quickly upon addition of heparin if desired (FIG. 5B). This is important for practical use of the gel because it avoids preparation of fresh dispersion every time. As a drug delivery system, the gel will contact with physiological fluid after injection. This will potentially affect the viscoelastic properties, which might in turn influence the release kinetics of the payloads. Thus the gel stability and properties were further examined by incubating a freshly made heparin-LAPONITE® gel with excessive biological saline and cell medium (EBM-2, Lonza, Walkersville, Md.). The angular frequency sweep measurements indicate that little impacts are caused on the viscoelastic properties of the gel by either saline or EBM-2 over different incubation time (FIG. 6A, B). In addition, pH condition on the gelation behavior is also examined using LAPONITE® dispersion prepared in deionized water with pH levels ranged from 2.8 to 10.6. When mixing with heparin, all LAPONITE® dispersions show similar gelation behavior and viscoelastic properties as confirmed by oscillatory time sweep measurements (FIG. 6C). Furthermore, the effects of ionic strength on gelation kinetics were also investigated to examine if the presence of salt ions will inhibit or retard gelation process.

The heparin was dissolved in NaCl solution and then added dropwise to LAPONITE® dispersion to yield heparin-LAPONITE® gels (7.6+19 mg/mL) containing 0.1 to 0.9 wt. % NaCl. The oscillatory time sweep measurements show that the presence of suitable amount of salt ions promoted the gelation process, instead of inhibiting or retarding gelation (FIG. 7). The G' and G" are increased gradually and almost tripled as the NaCl content increases from 0 to 0.9 wt. %. This is because the addition of salts reduces the thickness of the electrical double layer on the LAPONITE® surfaces, promoting gel formation. In this case, the anionic heparin together with the NaCl salts facilitated gelation kinetics with increased moduli at the tested content range. All these studies further confirmed the robust gelation ability between heparin and LAPONITE® to yield a stable gel for applications.

Figure 8:
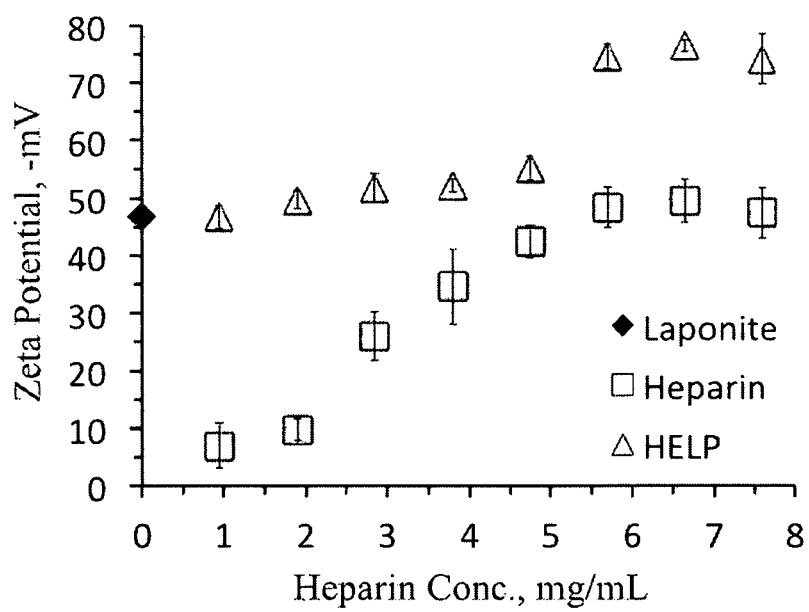
FIG. 8. Zeta potential measurements of LAPONITE®, heparin and heparin-LAPONITE® complexes as a function of heparin concentration. (Filled Diamond) LAPONITE® control at 9.5 mg/mL, (Square) heparin solutions from 0.95 to 7.6 mg/mL, and (Triangle) heparin-LAPONITE® complexes are comprised of heparin and LAPONITE® with concentrations ranged from 0.95+9.5 to 7.6+9.5 mg/mL. The H/L ratio of the heparin-LAPONITE® complexes is same to the heparin-LAPONITE® gels ranged from 1:10 to 8:10. The heparin-LAPONITE® complexes show a saturating absorption at heparin concentration between 4.75 to 5.7 mg/mL (H/L, 5:10 to 6:10). Above this threshold, more free heparin molecules contribute to the zeta potential values with a similar trend as the heparin control shows.

Zeta Potential to Examine the Electrostatic Interactions:

We believe that electrostatic interactions crosslink heparin and LAPONITE®, thus zeta potential was used to examine the change of charge upon mixing the two components (FIG. 8). In this case, the LAPONITE® concentration was 9.5 mg/mL, so that it can complex heparin without forming a gel. The latter will hinder the mobility of conductive components for zeta potential measurement. The heparin-LAPONITE® complex suspensions have concentrations (heparin+LAPONITE®) ranged from 0.95+9.5 to 7.6+9.5 mg/mL and the H/L ratio remained same to the heparin-LAPONITE® gels, ranged from 1:10 to 4:5. Compare to the zeta potential of heparin and LAPONITE® control, the Heparin-LAPONITE® complexes show little increase of zeta potential at heparin concentrations between 0.95 to 4.75 mg/mL (H/L, 1:10 to 1:2), followed by a sharp increase between 4.75 to 5.7 mg/mL (H/L, 1:2 to 3:5) and then a plateau between 5.7 to 7.6 mg/mL (H/L, 3:5 to 4:5). Such zeta potential profile indicates that most of the negatively charged heparin molecules are bound to the positively charged LAPONITE® edges at H/L ratio between 1:10 to 5:10. Few free heparins contribute to the zeta potential values at this range. The sharp increase of ZP implies a saturating absorption of heparin to LAPONITE® occurred at H/L ratio between 1:2 to 3:5. Above this threshold, more free heparin molecules contribute to zeta potential value in a similar trend as the heparin solution control shows (FIG. 8). Here, the saturating absorption occurs at H/L ratio between 1:2 to 3:5, which is slightly higher than that determined by rheological study at 1:2 (FIG. 3D). In that case of heparin-LAPONITE® gel, the two components quickly form network structure, and some of the anchored heparin chains are shared by the adjacent particles to form crosslinks. Thus it shows a slightly lower H/L ratio for the saturating absorption compared to the heparin-LAPONITE® complex. Nonetheless, the zeta potential measurement provides a good evidence for the proposed crosslinking mechanism based on electrostatic interactions between heparin and LAPONITE® edges.

Controlled Release of Protein and Protection from Proteolytic Degradation:

Most free growth factors degrade quickly in vivo by proteolytic cleavage, leading to low therapeutic efficacy. The advantages of the heparin-LAPONITE® delivery platform are the protection against proteolysis and sustained release of the proteins in an active form. This is demonstrated using FGF2 as a model biomolecule to investigate its release kinetics and stability with regard to proteolytic degradation (FIG. 9).

The FGF2 is loaded in heparin-LAPONITE® gels with H/L ratios of 1:5, 2:5 and 4:5. The H/L ratio is varied to compare the effects on its release kinetics. Same amount of free FGF2 is directly loaded in LAPONITE® gels with concentrations at 22.8 and 26.6 mg/mL as controls. The release profiles show that the cumulative release is elevated from 25.3±4.7% to 105±11% over 34 days when the H/L ratio increases from 1:5 to 2:5, but is reduced to 22.6±0.2% again when the H/L ratio is further increased to 4:5. However, both LAPONITE® controls show negligible FGF2 release (0.8±0.2 and 1.3±0.3%) over 34 days. Such release kinetics is mainly dependent on the binding between FGF2, heparin and LAPONITE®. In Heparin-LAPONITE® gels, FGF2 is complexed with heparin to form heparin-binding proteins and then incorporated in the gels (FIG. 3A). When at low H/L ratio of 1:5, the heparin-FGF2 complex is more easily absorbed onto LAPONITE® edges via electrostatic interaction, showing a slower and steadier release compared to the one with the H/L ratio at 2:5. Contrary to initial expectations, the gel with higher H/L ratio at 4:5 results in a slower release again, instead of faster release. It was suspected that this is mainly due to more free heparin molecules interacting with FGF2 to retain the latter within the gel, thus decreasing the release rate. When the free FGF2 is loaded in the LAPONITE® controls, the FGF2 molecules are directly bound to the nanoplatelets through hydrogen bonding, electrostatic interaction and physical absorption. The strong bounds fix the protein in the gel leading to very low levels of release.

The ability of heparin-LAPONITE® gel to protect FGF2 against proteolysis is examined by Western blot (FIG. 9B, C). The FGF2 released from Heparin-LAPONITE® gel over 134 h at 37° C. was collected for Western blot assay, which was compared to free FGF2 and heparin-FGF2 complex controls. After incubating with protease (trypsin) for 0.5 and 2 h, the FGF2 released from the Heparin-LAPONITE® gel (490 ng/mL determined by ELISA assay), showing band intensity similar to the heparin-FGF2 complex control, while the free FGF2 was completely digested by trypsin treatment within 0.5 h (FIG. 9B). This result demonstrates effective protection of the FGF2 from protease degradation and indicates that the released FGF2 is probably bound to heparin, rather than in the free form. The FGF2 released from LAPONITE® control and hyaluronic acid-LAPONITE® gel (HA-LAPONITE®) is also examined for comparison with Heparin-LAPONITE® gel (FIG. 9C). HA-LAPONITE® is prepared as a representative example to compare to the Heparin-LAPONITE® gel for protein delivery (Divya Bhatnagar D X, et al. Hyaluronic Acid and Gelatin Clay Composite. Journal of Chemical and Biological Interfaces. 2014; 2:1-11). Neither LAPONITE® nor HA-LAPONITE® gel could yield detectable FGF2 even before trypsin treatment. This is mainly due to very low release of FGF2 from both LAPONITE® and HA-LAPONITE® gels as determined by ELISA assay (~9.0 and 9.6 ng/mL FGF2 released, 0.090% and 0.096% cumulative release over 134 h). This result implies that FGF2 in HA-LAPONITE® gel is released in a similar way as compared to the LAPONITE® control. This is possibly because most, if not all, of the proteins bind directly to the LAPONITE® nanoplatelets because the hyaluronic acid has low affinity for FGF2, leading to extremely low dissociation of FGF2 from HA-LAPONITE® gel and likely no protection from enzymatic degradation as well. The comparison among Heparin-LAPONITE®, LAPONITE® and HA-LAPONITE® gels further demonstrated the versatility of Heparin-LAPONITE® gel for controlled release of bioactive proteins.

Figure 10:
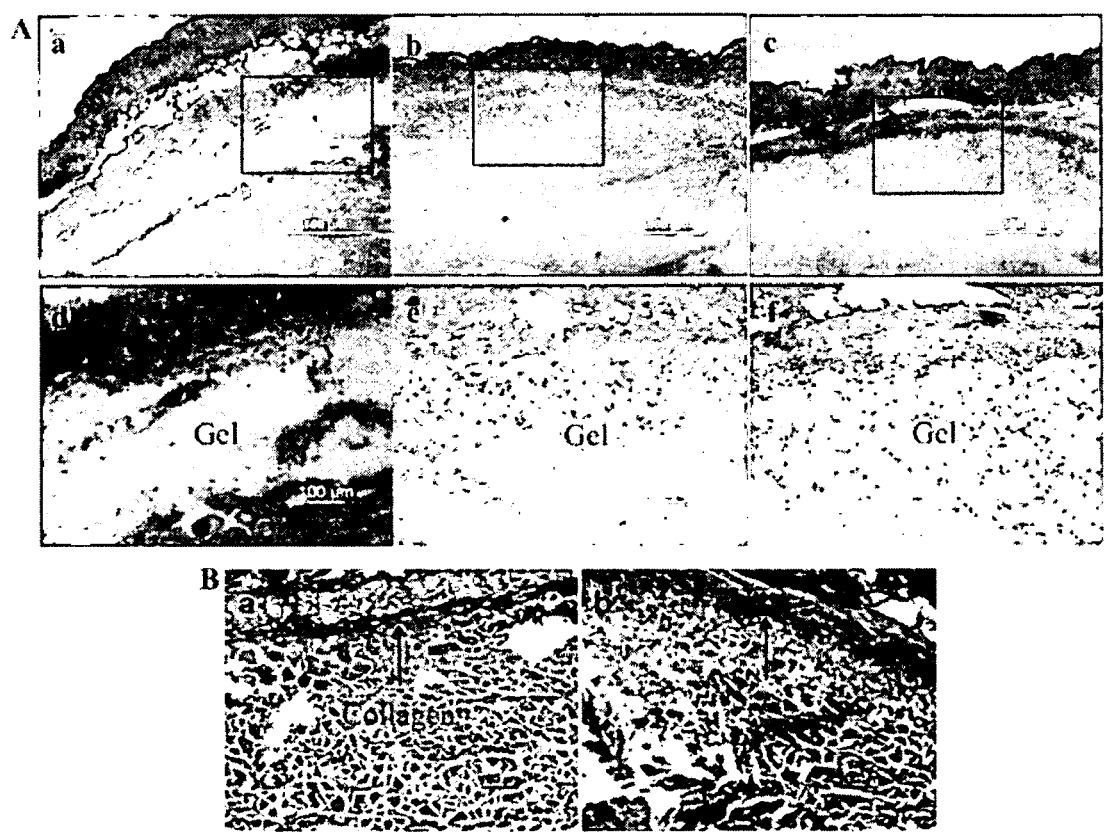
FIG. 10. (A) Micrographs of the H&E stained sections surrounding the injected heparin-LAPONITE® gel. Low magnification of images of the H&E stained tissues harvested at days (a) 3, (b) 14 and (c) 28, (Scale bar, 500 μm). Rectangular frames indicate the region chosen for higher magnifications (d-f), (Scale bar, 100 μm). (B) MTS stained tissues illustrate collagen deposition (arrow) after heparin-LAPONITE® injection at days (a) 14 and (b) 28, (Scale bar, 100 μm).

In Vive Biocompatibility Study:

Heparin-LAPONITE® gel with an H/L ratio at 2:5 (7.6+19 mg/mL) was selected as a representative for subcutaneous implantation study to investigate the host response. All animals survived throughout the study without any malignancy, infection or abscess observed at the injection sites. Tissues around the gel showed no adverse reactions such as necrosis, fibrosis and muscle degeneration (FIG. 10A). H&E staining showed phagocytic inflammatory infiltrates near the gel at day 3 post-injection (FIG. 10A(a, d)). The inflammatory infiltrates reduce significantly at week 2 post-injection and phagocytic cells migrate into and proliferate inside the gel (FIG. 10A(b, e)). Most of the macrophages migrated into the gel at week 4 (FIG. 10A(c, f)). The surrounding tissue was spared from inflammation throughout the study period. MTS staining shows a relatively loose layer of collagen and minimal deposition on the surface of the gel at week 2 and 4 post-injection (FIG. 10B). It is known that the inflammatory response to implanted biomaterials activates the immune cells (e.g. macrophages) to initiate the production of inflammatory cytokines and chemokines. These secreted peptides typically recruit more immune cells to the implantation site. Here, the recruited cells appear to accumulate on gel edge and then migrate into the gel.

Figure 11:
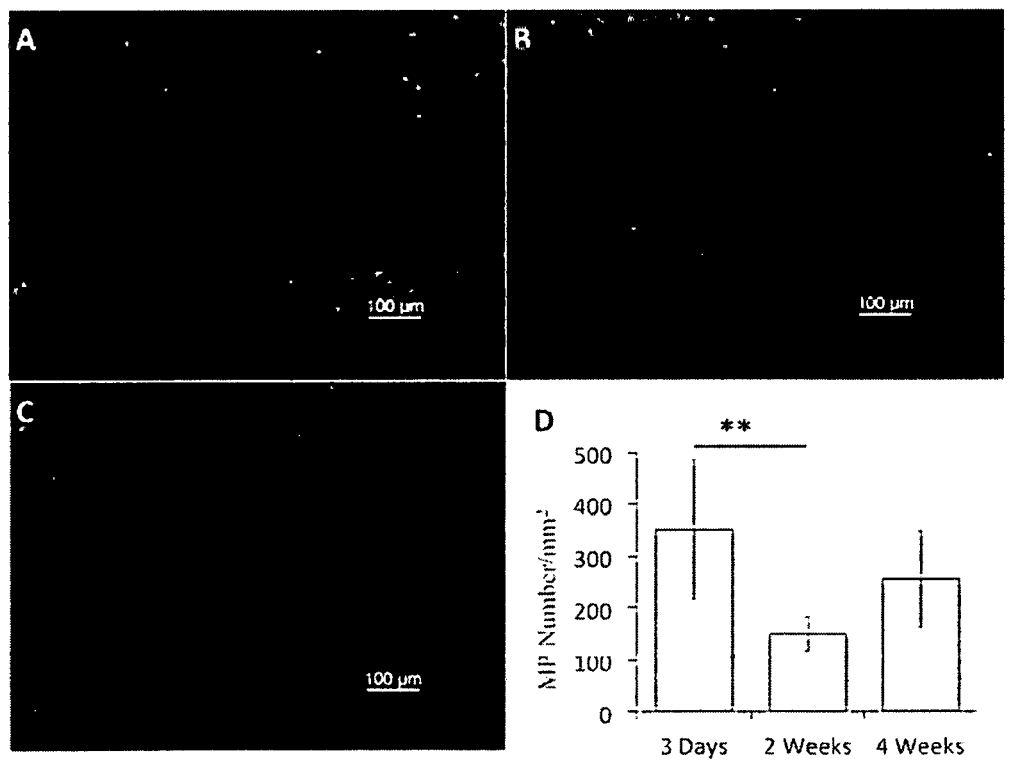
FIG. 11. Representative micrographs of immunohistochemically stained sections of CD68 positive macrophages merged with DAPI staining (Scale bar, 100 μm). Tissues were harvested at days (A) 3, (B) 14 and (C) 28. (D) The number of CD68 positive macrophages (MP number per $mm^2$) at different time points. The population of CD68+ cells decreases significantly from day 3 to week 2, and may have slightly increased from 2 to 4 weeks, however, the difference is not statistically significant. Images from more than 5 random areas around the injection site are used for quantification. ** P=0.0067, P<0.05 is considered significant. Data represent mean±SD (n≥5).

To further investigate cell activities, CD68 and DAPI were used to detect macrophages distribution relative to the subcutaneous implants. CD68 is a pan-macrophage marker. By day 3 after injection, the tissue adjacent to the gel contained most inflammatory cells, as revealed by CD68 staining. This is attributed to a non-specific inflammatory response to the material, which has been widely observed in many implanted biomaterials. At week 2, there was a significant reduction in newly-recruited macrophages compared to day 3 (FIG. 11A, B), indicating that inflammation close to the surface of the gel was resolved at week 2. On the other hand, the inflammatory cells inside the gel increased, but not significantly, at week 4 post-injection (FIG. 11B, C, D). Most likely the gel degraded sufficiently to allow cell infiltration deeper into the gel.

Figure 12:
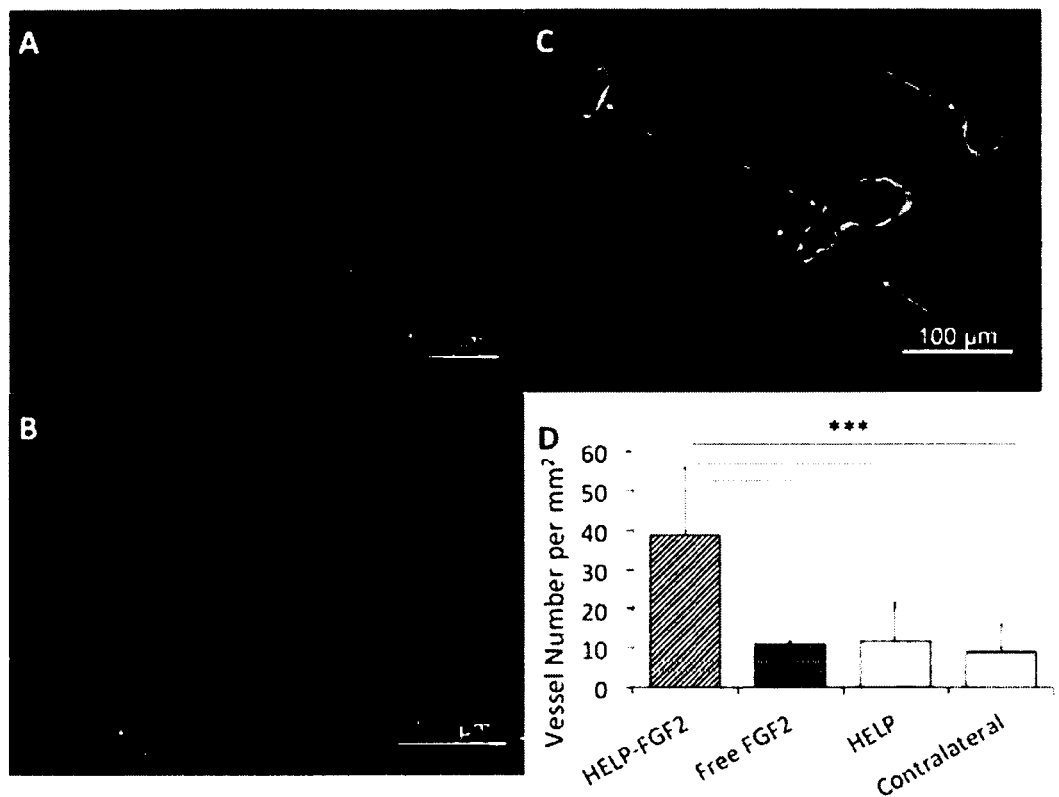
FIG. 12. Potent angiogenesis induced by sustained release of FGF2 from heparin-LAPONITE® gel. (A-C) Representative confocal micrographs show the distribution of blood vessels in tissues marked by CD31 and SMA staining (originals in color) (Scale bar, 100 μm). The tissues were harvested at 2 weeks after injection with (A) heparin-LAPONITE® alone, (B) the contralateral tissue without gel implantation as a control, and (C) FGF2-loaded heparin-LAPONITE® gel. Compare with heparin-LAPONITE® gel alone and its contralateral, FGF2-loaded heparin-LAPONITE® gel efficiently induces generation of more mature blood vessels by the sustainably released FGF2. (D) Comparison of blood vessel number per unit area in the tissues adjacent to the implantation site. The blood vessel number per square millimeter is calculated by counting the vessel number over the area. The free FGF2 control is adopted from a previous study conducted by the same person (Chu H, et al., Injectable fibroblast growth factor-2 coacervate for persistent angiogenesis. Pmroc. Nat'l. Acad. Sci. U.S.A. 2011; 108:13444-9). Images from 10-20 random areas around the injection site are used for quantification. One-way ANOVA followed by Bonferroni correction, ***P<0.0001, P<0.05 is considered significant. Data represent mean±SD.

FGF2-Loaded Heparin-LAPONITE® Gel Induces Strong Angiogenesis:

In order to examine the bioactivity of the proteins released from the gel, FGF2 was chosen as a model drug, and angiogenesis as a readout of FGF2 activity. Therapeutic angiogenesis is a potential treatment for many human diseases such as coronary and peripheral ischemia (Chu H, et al. *Proc. Nat'l. Acad. Sci. U.S.A.* 2011; 108:13444-9 and Gupta R, et al. Human studies of angiogenic gene therapy. *Circ. Res.* 2009; 105:724-36). The FGF2-loaded Heparin-LAPONITE® gel (Heparin-LAPONITE®-FGF2) and Heparin-LAPONITE® alone were subcutaneously injected in the back of BALB/cJ mice. The tissues surrounding the implantation site and the contralateral side without gel treatment were harvested at different time points to study the effects of the released FGF2 on angiogenesis. The mature blood vessel formation was confirmed by co-staining of CD31 (endothelial cell marker) and α-smooth cell actin (SMA, a mural cell marker). Compared to the heparin-LAPONITE® alone treated group and the contralateral control, the heparin-LAPONITE®-FGF2 gel-treated group generated more mature blood vessels with larger diameter (FIG. 12A-C). Whereas the heparin-LAPONITE® alone group showed no significant difference compared to its contralateral control (FIG. 12A, B). These results indicate that the released FGF2 from heparin-LAPONITE®-FGF2 gel plays a significant role in promoting the formation of mature blood vessels. To further compare the blood vessel number induced by heparin-LAPONITE®-FGF2 gel, heparin-LAPONITE® alone and the contralateral control, the blood vessel number per square millimeter was quantified by randomly selecting 10-20 images surrounding the implantation site (FIG. 12D). The number of mature blood vessels per unit area induced by heparin-LAPONITE®-FGF2 gel was more than 3 times to that of the contralateral control. Compare to the contralateral control, the heparin-LAPONITE® alone treatment cannot induce angiogenesis at 2 weeks post-injection. Furthermore, prior studies showed that free FGF2 treatment only demonstrated a limited angiogenesis due to the short half-life in vivo (FIG. 12D) (Chu H, et al., *Proc. Nat'l. Acad. Sci. U.S.A.* 2011; 108:13444-9). The significantly enhanced angiogenesis indicates a well preserved bioactivity of the released FGF2 from heparin-LAPONITE® gel.

Figure 13:
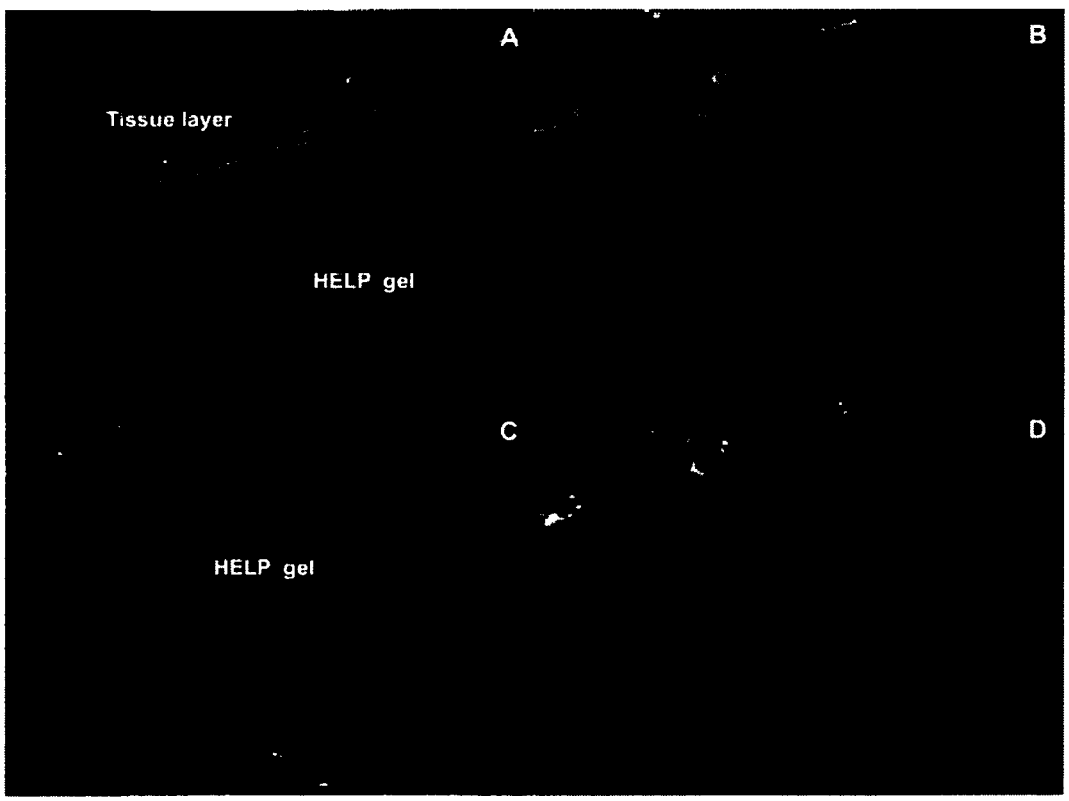
FIG. 13 (original in color). Representative microscopic images of the merged CD31, SMA and DAPI stained sections show cell activities of endothelial and smooth muscle cells induced by the heparin-LAPONITE® gel implantation. (A) 2 weeks and (C) 4 weeks post-injection (Scale bar 500 μm). (B and D) are the corresponding higher resolution images of the selected rectangular area (Scale bar. 100 μm). Compare to that of 2 weeks post-injection, a significant amount of endothelial cells and smooth muscle cells are recruited toward the implanted gel at 4 weeks after injection. These cells trend to migrate from gel edge to center. The two cells accumulated on some areas of the gel edge show angiogenesis. The gel shows less dense at 4 weeks post-injection, indicating the gel degradation by the recruited cells.
Figure 14:
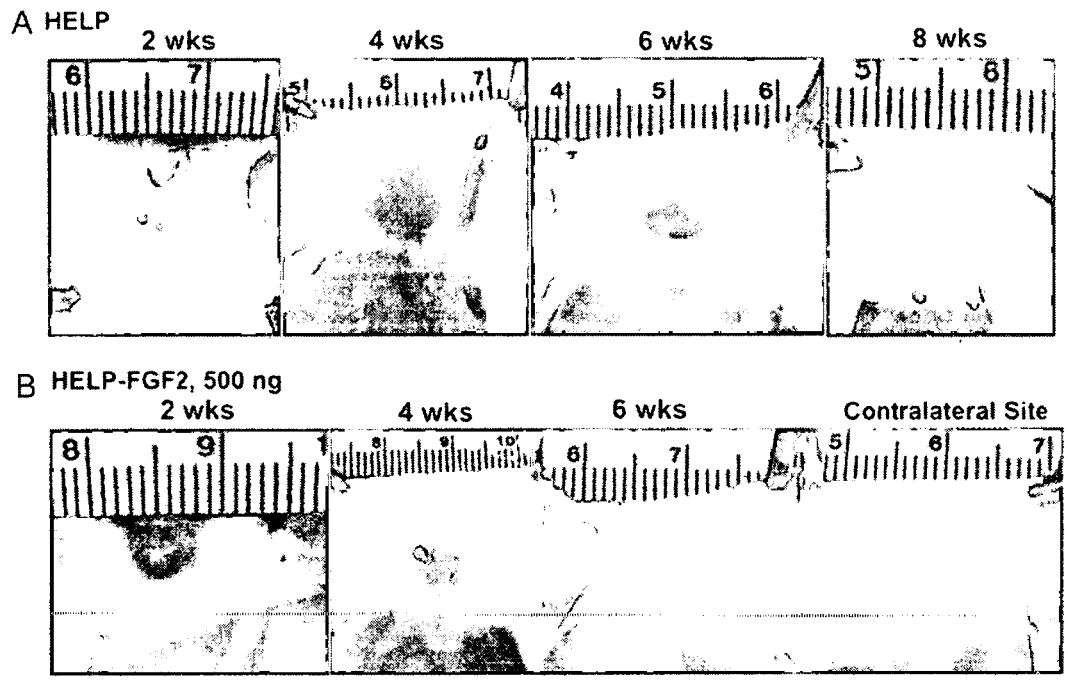
FIG. 14. In vivo biodegradation of heparin-LAPONITE® gel with or without FGF2 by subcutaneous implantation for 8 weeks. (A) heparin-LAPONITE® gel alone is gradually degraded in 8 weeks. (B) FGF2-loaded heparin-LAPONITE® gel is degraded in about 6 weeks. 100 μL of heparin-LAPONITE® gel with or without FGF2 (500 ng) was injected in the back of BALB/cJ mice. Without growth factor, the gel is gradually degraded in 8 weeks without causing mouse death, any malignant infection, or abscess at the injection sites. When loading with FGF2, the material is degraded in about 6 weeks. The growth factor facilitated cell recruitments into the gel and promoted its degradation rate.

The FGF2-loaded Heparin-LAPONITE® gel shows faster in vivo degradation than heparin-LAPONITE® alone because the cells are more quickly recruited into the gel (FIG. 13). The heparin-LAPONITE®-FGF2 gel was nearly completely degraded in 6 weeks after injection, about 2 weeks faster than heparin-LAPONITE® alone (FIG. 14). The accelerated cell recruitments and gel degradation should facilitate the applications of this gel because this study indicates that angiogenesis can be achieved within 2 weeks and fast gel degradation after that would minimize foreign body response.

In sum, a versatile injectable hydrogel was designed for bioactive protein delivery with stabilized molecular structure and preserved bioactivity for tissue regeneration. This gel is made from heparin solution and LAPONITE® dispersion by simply mixing the two components at appropriate ratio by manually swirling for one minute. FGF2 is used as an example for in vitro and in vivo studies to investigate its release kinetics, stability against proteolytic degradation and bioactivity for angiogenesis. This delivery system is versatile and is expected to be useful for protection and therapeutic delivery of many other proteins as well. More than 400 proteins and peptides bind with heparin.

Example 2

This example illustrates the robust gelation ability between LAPONITE® and ionic amino acid molecules, cationic lysine and anionic glutamic acid. The easy gelation using various cationic, anionic and hydrophilic molecules with LAPONITE® is expected to expand the applications as versatile drug delivery vehicles because different cargos can choose different cationic, or anionic, or hydrophilic molecules to complex and incorporate into the gel for sustainable release.

Here, small biomolecules such as cationic and anionic amino acids are used to further examine the rapid gelation with LAPONITE® dispersion. Two types of amino acids are used as the representatives of small molecular gelators. One is cationic lysine (K) and the other is anionic glutamic acid (E). The K is readily dissolved in deionized water to form solutions with concentrations ranged from 20 to 100 mg/mL for use. E is less soluble in pure deionized water, so it requires using 0.13 M and 0.65 M NaOH solution to dissolve the amino acid to yield clear E solutions (20 and 100 mg/mL) for use.

Figure 15:
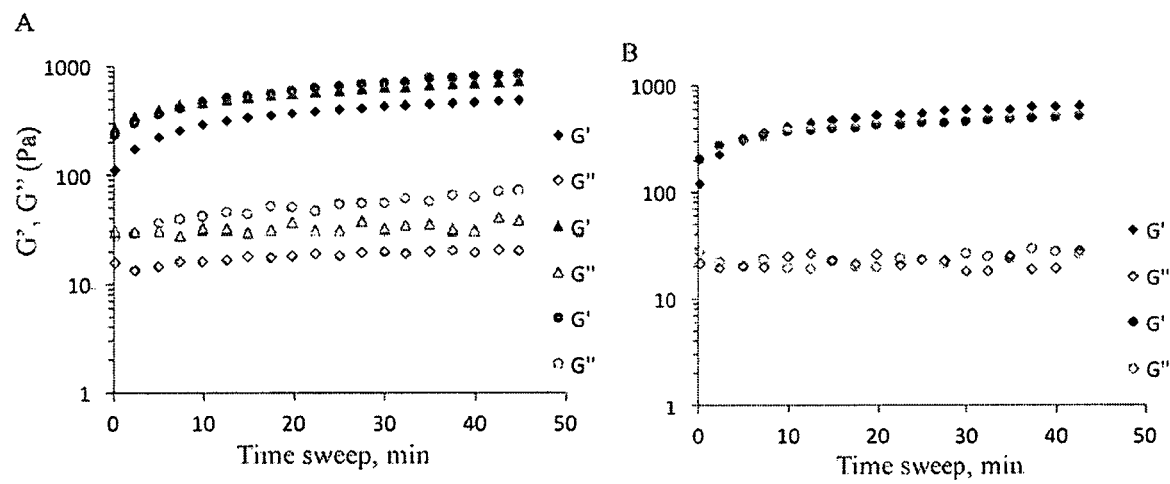
FIG. 15. Oscillatory time sweep measurements of LAPONITE® dispersion gelled with cationic and anionic molecules, (A) Lysine and (B) Glutamic acid. The LAPONITE® concentration is fixed at 19 mg/mL, while the concentrations of lysine or glutamic acid are varied. (Diamond) 19+0.95 mg/mL (20:1), (Triangle) 19+2.4 mg/mL (8:1) and (Circle) 19+4.8 mg/mL (4:1).

0.1 mL of K or E solution was added to 2 mL of LAPONITE® dispersion (20 mg/mL) and manually swirled for couple of seconds to form LAPONITE®-K and LAPONITE®-E mixtures. The mixtures were immediately transferred to a parallel plate for oscillatory rheometry tests. FIG. 15 shows the gelation kinetics of LAPONITE®-K and LAPONITE®-E as a functional of time. It shows that both E and K can quickly gel with LAPONITE® dispersion. It is believed that K (cationic amino acid) molecules interact with negative charges on LAPONITE® platelet faces to promote gelation; while E (anionic amino acid) molecules interact with positive charges on LAPONITE® edge to facilitate gelation process. An exemplary weight ratio range of LAPONITE®-K for gelation is between 20:1 to 4:1, and the gelation rate is proportional to the K fraction. Beyond the ratio of 4:1, LAPONITE®-K forms cloudy viscous mixture with a reduced storage modulus. For LAPONITE®-E, the weight ratio can be increased above 4:1, but further increase of E fraction will not contribute to either gelation rate or storage modulus.

LAPONITE® was reported as carriers for delivery of amino acids (M. Ghadiri, et al. Layered silicate clay functionalized with amino acids: wound healing application, *RSC Advances,* 2014, 4, 35332), but these experiments revealed that these ionic molecules can be employed as efficient gelators (gelling agents) to gel with LAPONITE® via ionic interactions. In addition to lysine and glutamic acid, as the representatives of cationic and anionic molecules to demonstrate the quick gelation with LAPONITE®, other ionic amino acids such as arginine and aspartic acid, and hydrophilic amino acids, including glutamine, histidine, asparagine, serine, tyrosine, threonine and other water soluble amino acids; cationic oligopeptides such as the dimer, trimer, tetramer, pentamer and hexamer, etc. of the above mentioned cationic amino acids; anionic oligo-peptides and polypeptide of above mentioned anionic amino acids; and hydrophilic oligo-peptides and polypeptides of above mentioned hydrophilic amino acids. Above, heparin is shown as a representative of sulfated or sulfamated polymers to gel with LAPONITE®. Together, all these shear thinning hydrogels formed between ionic biomolecules and LAPONITE® can expand the versatility of this technique for drug delivery applications.

The following clauses illustrate various aspects of the invention:
1. A shear-thinning therapeutic composition, comprising:
   a. silicate platelets;
   b. a gelling agent non-covalently linking the platelets to form a shear-thinning composition; and
   c. a therapeutic agent that binds non-covalently to the gelling agent and that is complexed non-covalently with the gelling agent.
2. The composition of clause 1, wherein the gelling agent is a sulfated or sulfamated polymer.
3. The composition of clause 2, wherein the sulfated or sulfamated polymer is a sulfated glycosaminoglycan.
4. The composition of clause 3, wherein the sulfated glycosaminoglycan is heparin or heparan sulfate.
5. The composition of any one of clauses 1-4, wherein the therapeutic agent is a member of the heparin interactome.
6. The composition of clause 2, wherein the sulfated or sulfamated polymer is a polysaccharide.
7. The composition of any one of clauses 2-5, wherein the therapeutic agent binds specifically to the sulfated or sulfamated polymer.
8. The composition of any one or clauses 2-5, wherein the therapeutic agent binds non-specifically to the sulfated or sulfamated polymer.
9. The composition of clause 1, wherein the gelling agent is one or more of a cationic amino acid; an anionic amino acid; a hydrophilic amino acid; and a cationic, anionic, or hydrophilic polypeptide, and optionally the gelling agent is a cationic oligopeptide comprising from 2 to 10 amino acids or from 2 to 6 amino acids.
10. The composition of clause 9, wherein the gelling agent is a cationic oligopeptide of from 2 to 10 amino acids, optionally from 2 to 6 amino acids.
11. The composition of clause 9, wherein the gelling agent is a homopolymer.
12. The composition of clause 9, wherein the cationic, anionic, or hydrophilic amino acids are lysine, arginine, glutamic acid, aspartic acid, glutamine, histidine, asparagine, serine, tyrosine, or threonine.
13. The composition of any one of clauses 1-11, wherein the silicate platelets comprise hydrous sodium lithium magnesium silicate platelets, such as LAPONITE® platelets.
14. The composition of any one or clauses 1-13, wherein the therapeutic agent is an oligopeptide, a polypeptide or a protein.
15. The composition of any one or clauses 1-14, wherein the therapeutic agent is a growth factor.
16. The composition of any one or clauses 1-15, wherein the therapeutic agent is Fibroblast Growth Factor 2 (FGF-2).
17. The composition of any one of clauses 1-16, wherein:
   a. the ratio of therapeutic agent to the sulfated or sulfamated polymer and/or to the gelation agent ranges from 1:16000 to 1:1 by weight, from 1:8000 to 1:3 by weight, or from 1:1520 up to 1:3 by weight;
   b. the ratio of the sulfated or sulfamated polymer and/or to the gelling agent ranges to the silicate platelets ranges from 1:10 to 1:1 by weight, or from 1:10 to 1:2 by weight; and/or
   c. the concentration of the silicate platelets ranges from 10 mg/mL to 80 mg/mL (1% to 8%), or from 15 mg/mL to 50 mg/mL (1.5% to 5.0%).
18. A method of making a composition for delivery of a therapeutic agent, comprising:
   a. mixing a gelling agent with a therapeutic agent that is a binding partner of gelling agent to produce a complex of the gelling agent and the therapeutic agent; and
   b. mixing the complex of the gelling agent and the therapeutic agent with silicate platelets to produce a shear-thinning hydrogel.
19. The method of clause 18, wherein the gelling agent is a sulfated or sulfamated polymer.
20. The method of clause 19, wherein the sulfated or sulfamated polymer is a sulfated glycosaminoglycan.
21. The method of clause 19 or 20, wherein the therapeutic agent binds specifically to the sulfated or sulfamated polymer.
22. The method of clause 19 or 20, wherein the therapeutic agent binds non-specifically to the sulfated or sulfamated polymer.
23. The method of clause 20, wherein the sulfated glycosaminoglycan is heparin or heparan sulfate.
24. The method of clause 23, wherein the therapeutic agent is a member of the heparin interactome.
25. The method of clause 18, wherein the gelling agent is one or more of a cationic amino acid; an anionic amino acid; a hydrophilic amino acid; and a cationic, anionic, or hydrophilic polypeptide, and optionally the gelling agent is a cationic oligopeptide comprising from 2 to 10 amino acids or from 2 to 6 amino acids.
26. The method of clause 25, wherein the gelling agent is a cationic oligopeptide of from 2 to 10 amino acids, optionally from 2 to 6 amino acids.
27. The method of clause 25, wherein the gelling agent is a homopolymer.
28. The method of clause 25, wherein the cationic, anionic, or hydrophilic amino acids are lysine, arginine, glutamic acid, aspartic acid, glutamine, histidine, asparagine, serine, tyrosine, or threonine.
29. The method of any one of clauses 25-28, wherein the gelling agent is a poly(glutamic acid) or poly(aspartic acid) oligomer of from 2 to 10, or from 2 to 6 amino acids.
30. The method of any one of clause 18-29, wherein the silicate platelets comprise hydrous sodium lithium magnesium silicate platelets, such as LAPONITE® platelets.
31. The method of any one or clauses 18-30, wherein the therapeutic agent is an oligopeptide, a polypeptide or a protein.
32. The method of any one or clauses 18-30, wherein the therapeutic agent is a growth factor.
33. The method of any one or clauses 18-30, wherein the therapeutic agent is Fibroblast Growth Factor 2 (FGF-2).
34. The method of any one or clauses 18-33, wherein:
   a. the ratio of therapeutic agent to the gelling agent, or to the sulfated or sulfamated polymer ranges from 1:16000 to 1:1 by weight, from 1:8000 to 1:3 by weight, or from 1:1520 up to 1:3 by weight;

b. the ratio of the gelling agent, or the sulfated or sulfamated polymer to the silicate platelets ranges from 1:10 to 1:1 by weight, or from 1:10 to 1:2 by weight; or
c. the concentration of the silicate platelets ranges from 10 mg/mL to 80 mg/mL (1% to 8%), or from 15 mg/mL to 35 mg/mL (1.5% to 5.0%).
35. The method of any one or clauses 18-33, wherein:
a. the ratio of therapeutic agent to the gelling agent, or to the sulfated or sulfamated polymer ranges from 1:16000 to 1:1 by weight, from 1:8000 to 1:3 by weight, or from 1:1520 up to 1:3 by weight;
b. the ratio of the gelling agent, or the sulfated or sulfamated polymer to the silicate platelets ranges from 1:10 to 1:1 by weight, or from 1:10 to 1:2 by weight; and
c. the concentration of the silicate platelets ranges from 10 mg/mL to 80 mg/mL (1% to 8%), or from 15 mg/mL to 50 mg/mL (1.5% to 5.0%).
36. A method of administering a therapeutic agent to a patient, comprising administering a shear-thinning therapeutic hydrogel according to any one of clauses 1-17 to a patient.
37. The method of clause 36, wherein the shear-thinning therapeutic hydrogel is administered parenterally at a location in the patient of an injury or defect, to promote tissue growth, differentiation, and/or repair of the injury or defect.
38. A method of inducing angiogenesis in a patient, comprising administering to a patient an amount of the composition of clause 1-17 effective to induce angiogenesis in a patient, wherein the therapeutic agent is an angiogenic agent.
39. The method of clause 38, wherein the angiogenic agent is chosen from: erythropoietin (EPO), basic fibroblast growth factor (bFGF), acidic fibroblast growth factor (aFGF), fibroblast growth factor-2 (FGF-2), granulocyte colony stimulating factor (G-CSF), granulocyte macrophage colony stimulating factor (GM-CSF), hepatocyte growth factor (HGF), insulin-like growth factors 1 and 2 (IGF-1 and IGF-2), placental growth factor (PIGF), platelet derived growth factor (PDGF), stromal derived factor 1 alpha (SDF-1 alpha), and vascular endothelial growth factor (VEGF), angiopoietins (Ang 1 and Ang 2), matrix metalloproteinase (MMP), delta-like ligand 4 (Dll4), and class 3 semaphorins (SEMA3s), among the others.
40. A method of filling a soft tissue in a patient, comprising injecting or implanting in a patient the composition of any one of clauses 1-17.

While the present invention is described with reference to several distinct embodiments, those skilled in the art may make modifications and alterations without departing from the scope and spirit. Accordingly, the above detailed description is intended to be illustrative rather than restrictive.

We claim:

1. A shear-thinning therapeutic composition, comprising:
   silicate platelets;
   a gelling agent non-covalently linking the platelets to form a shear-thinning composition; and
   a therapeutic agent that binds non-covalently to the gelling agent and that is complexed non-covalently with the gelling agent wherein the gelling agent is a sulfated or sulfamated polymer, polysaccharide, or glycosaminoglycan.

2. The composition of claim 1, wherein the sulfated glycosaminoglycan is heparin, heparan sulfate, or a member of the heparin interactome.

3. The composition of claim 1, wherein:
   the ratio of therapeutic agent to the sulfated or sulfamated polymer, polysaccharide, or glycosaminoglycan ranges from 1:16000 to 1:1 by weight, from 1:8000 to 1:3 by weight, or from 1:1520 up to 1:3 by weight; or
   the ratio of the sulfated or sulfamated polymer, polysaccharide, or glycosaminoglycan and/or to the gelling agent ranges to the silicate platelets ranges from 1:10 to 1:1 by weight, or from 1:10 to 1:2 by weight.

4. The composition of claim 1, wherein the therapeutic agent is a growth factor.

5. The composition of claim 1, wherein the silicate platelets comprise hydrous sodium lithium magnesium silicate platelets.

6. The composition of claim 1, wherein the therapeutic agent is an oligopeptide, a polypeptide or a protein.

7. The composition of claim 4, wherein the growth factor is Fibroblast Growth Factor 2 (FGF-2).

8. The composition of claim 1, wherein the concentration of the silicate platelets ranges from 10 mg/mL to 80 mg/mL (1% to 8%), or from 15 mg/mL to 50 mg/mL (1.5% to 5.0%).

9. A method of making a composition for delivery of a therapeutic agent, comprising:
   mixing a gelling agent with a therapeutic agent that is a binding partner of the gelling agent to produce a complex of the gelling agent and the therapeutic agent; and
   mixing the complex of the gelling agent and the therapeutic agent with silicate platelets to produce a shear-thinning hydrogel
   wherein the gelling agent non-covalently links the platelets and is a sulfated or sulfamated polymer, polysaccharide, or glycosaminoglycan; and
   wherein the therapeutic agent binds non-covalently to the gelling agent and is complexed non-covalently with the gelling agent.

10. The method of claim 9, wherein the sulfated or sulfamated polymer, polysaccharide, or glycosaminoglycan is heparin, heparan sulfate, or a member of the heparin interactome.

11. The method of claim 9, wherein the silicate platelets comprise hydrous sodium lithium magnesium silicate platelets.

12. The method of claim 9, wherein the therapeutic agent is an oligopeptide, a polypeptide or a protein.

13. The method of claim 9, wherein the therapeutic agent is a growth factor.

14. The method of claim 13, wherein the growth factor is Fibroblast Growth Factor 2 (FGF-2).

15. The method of claim 9, wherein:
   the ratio of therapeutic agent to the gelling agent ranges from 1:16000 to 1:1 by weight, from 1:8000 to 1:3 by weight, or from 1:1520 up to 1:3 by weight;
   the ratio of the gelling agent to the silicate platelets ranges from 1:10 to 1:1 by weight, or from 1:10 to 1:2 by weight; or
   the concentration of the silicate platelets ranges from 10 mg/mL to 80 mg/mL (1% to 8%), or from 15 mg/mL to 35 mg/mL (1.5% to 5.0%).

16. The method of claim 9, wherein:
   the ratio of therapeutic agent or to the sulfated or sulfamated polymer ranges from 1:16000 to 1:1 by weight, from 1:8000 to 1:3 by weight, or from 1:1520 up to 1:3 by weight; or
   the ratio of the gelling agent, or the sulfated or sulfamated polymer to the silicate platelets ranges from 1:10 to 1:1 by weight, or from 1:10 to 1:2 by weight.

17. The method of claim 9, wherein the concentration of the silicate platelets ranges from 10 mg/mL to 80 mg/mL (1% to 8%), or from 15 mg/mL to 50 mg/mL (1.5% to 5.0%).

18. The method of claim 9, wherein the shear-thinning therapeutic hydrogel is administered parenterally at a location in a patient of an injury or defect, to promote tissue growth, differentiation, and/or repair of the injury or defect.

19. A method of inducing angiogenesis in a patient, comprising administering to a patient an amount of the composition of claim 1 effective to induce angiogenesis in a patient, wherein the therapeutic agent is an angiogenic agent.

20. A method of filling a soft tissue in a patient, comprising injecting or implanting in a patient the composition of claim 1.

\* \* \* \* \*

UNITED STATES PATENT AND TRADEMARK OFFICE
CERTIFICATE OF CORRECTION

PATENT NO. : 11,077,051 B2  
APPLICATION NO. : 16/333627  
DATED : August 3, 2021  
INVENTOR(S) : Ding et al.

Page 1 of 1

It is certified that error appears in the above-identified patent and that said Letters Patent is hereby corrected as shown below:

On the Title Page

Column 2, item (56) Other Publications, Line 1, delete ""Ashear-" and insert -- A shear --

Column 2, item (56) Other Publications, Line 21, delete "LAPONITE"," and insert
-- LAPONITE®" --

In the Specification

Column 1, Line 11, before "which" insert -- each of --

In the Claims

Column 34, Line 61, Claim 16, after "agent" delete "or"

Signed and Sealed this
Fourteenth Day of June, 2022

Katherine Kelly Vidal
*Director of the United States Patent and Trademark Office*